(12) United States Patent
Toporek et al.

(10) Patent No.: US 12,214,174 B2
(45) Date of Patent: Feb. 4, 2025

(54) DATA COLLECTION DEVICE FOR ATTACHMENT TO AN INJECTION DEVICE

(71) Applicant: Sanofi, Paris (FR)

(72) Inventors: Maurice Toporek, Frankfurt am Main (DE); Michael Jugl, Frankfurt am Main (DE); Günther Sendatzki, Frankfurt am Main (DE); Oliver Charles Gazeley, Warwick (GB); Prasannah Nanayakkara, Warwick (GB); Aidan Michael O'Hare, Warwick (GB); Robert Veasey, Warwick (GB); David Aubrey Plumptre, Warwick (GB)

(73) Assignee: Sanofi, Paris (FR)

( * ) Notice: Subject to any disclaimer, the term of this patent is extended or adjusted under 35 U.S.C. 154(b) by 412 days.

(21) Appl. No.: 17/737,107

(22) Filed: May 5, 2022

(65) Prior Publication Data
US 2022/0265937 A1    Aug. 25, 2022

Related U.S. Application Data

(63) Continuation of application No. 16/466,478, filed as application No. PCT/EP2017/081490 on Dec. 5, 2017, now Pat. No. 11,357,920.

(30) Foreign Application Priority Data

Dec. 7, 2016 (EP) .................................... 16306633

(51) Int. Cl.
*A61M 5/315* (2006.01)
*A61M 5/31* (2006.01)

(52) U.S. Cl.
CPC .... *A61M 5/31528* (2013.01); *A61M 5/31551* (2013.01); *A61M 2005/3126* (2013.01);
(Continued)

(58) Field of Classification Search
None
See application file for complete search history.

(56) References Cited

U.S. PATENT DOCUMENTS

| 10,446,269 B2 | 10/2019 | Groeschke et al. |
| 2011/0313349 A1 * | 12/2011 | Krulevitch ............. G16H 20/17 604/65 |

(Continued)

FOREIGN PATENT DOCUMENTS

| CN | 104203315 | 12/2014 |
| CN | 105073165 | 11/2015 |

(Continued)

OTHER PUBLICATIONS

International Preliminary Report on Patentability in International Appln. No. PCT/EP2017/081490, dated Jun. 11, 2019, 9 pages.

(Continued)

*Primary Examiner* — Manuel A Mendez
(74) *Attorney, Agent, or Firm* — Fish & Richardson P.C.

(57) ABSTRACT

Data collection devices for attachment to injection devices are disclosed. In one embodiment, the data collection device includes: a body attachable to a dial member of the injection device, a sensor arrangement comprising a sensor and a scale, and a processor. The sensor is configured to detect a rotation of the body relative to a trigger of the injection device. The processor is configured to detect a rotation of the body relative to the trigger. One of the sensor and the scale is arranged in or on the body and wherein the other one of the sensor and the scale is located on the trigger or is rotationally lockable to the trigger configured to detect a rotation of the body relative to the trigger.

27 Claims, 11 Drawing Sheets

(52) U.S. Cl.
CPC ..... *A61M 5/31568* (2013.01); *A61M 5/31585* (2013.01); *A61M 2205/3306* (2013.01); *A61M 2205/3327* (2013.01)

(56) References Cited

U.S. PATENT DOCUMENTS

| | | | |
|---|---|---|---|
| 2013/0090603 A1 | 4/2013 | Hoyle, Jr. | |
| 2014/0350516 A1 | 11/2014 | Schwab et al. | |
| 2015/0018775 A1* | 1/2015 | Groeschke | A61M 5/31568 604/207 |
| 2015/0094667 A1 | 4/2015 | Verhoeven et al. | |
| 2015/0196714 A1 | 7/2015 | Creaturo | |
| 2015/0367077 A1 | 12/2015 | Plambech et al. | |
| 2016/0051760 A1 | 2/2016 | Krusell et al. | |
| 2016/0196714 A1 | 7/2016 | Vancura | |

FOREIGN PATENT DOCUMENTS

| | | |
|---|---|---|
| CN | 105307711 | 2/2016 |
| EP | 3103492 | 12/2016 |
| JP | 2006-519074 | 8/2006 |
| JP | 2012-519025 | 8/2012 |
| JP | 2014-516599 | 7/2014 |
| JP | 2015-506771 | 3/2015 |
| JP | 2016-506845 | 3/2016 |
| JP | 2018-517502 | 7/2018 |
| RU | 2004120786 | 4/2005 |
| WO | WO 2003/053503 | 7/2003 |
| WO | WO 2004/078239 | 9/2004 |
| WO | WO 2004/078240 | 9/2004 |
| WO | WO 2004/078241 | 9/2004 |
| WO | WO 2010/098927 | 9/2010 |
| WO | WO 2012/046199 | 4/2012 |
| WO | WO 2013/120778 | 8/2013 |
| WO | WO 2014/128157 | 8/2014 |
| WO | WO 2014/173434 | 10/2014 |
| WO | WO 2015/071211 | 5/2015 |
| WO | WO 2015/136513 | 9/2015 |
| WO | WO 2015/138093 | 9/2015 |
| WO | WO 2016/116566 | 7/2016 |
| WO | WO 2016/198516 | 12/2016 |

OTHER PUBLICATIONS

International Search Report and Written Opinion in International Appln. No. PCT/EP2017/081490, dated Feb. 26, 2018, 13 pages.

* cited by examiner

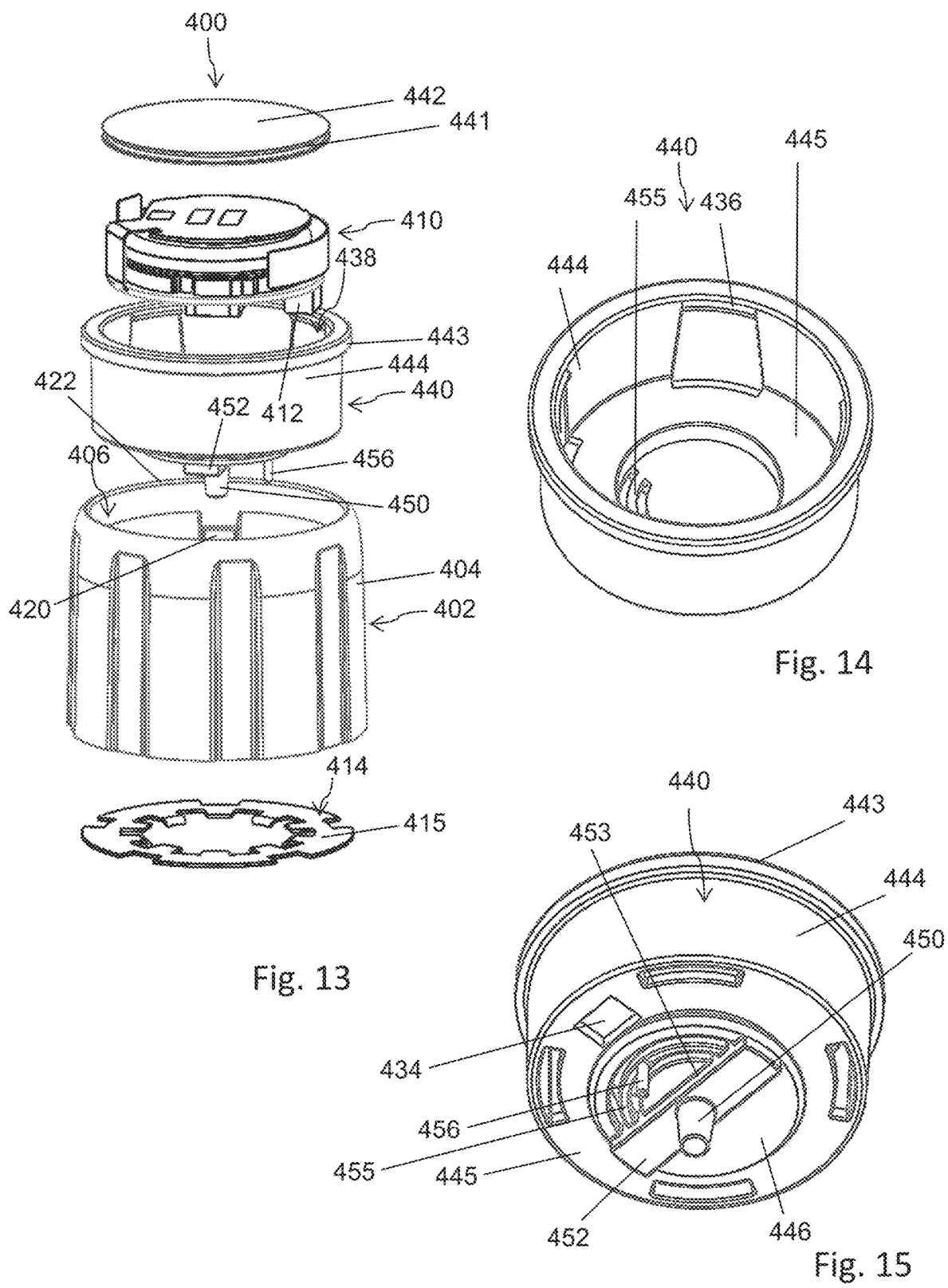

A-A

DATA COLLECTION DEVICE FOR ATTACHMENT TO AN INJECTION DEVICE

CROSS REFERENCE TO RELATED APPLICATIONS

The present application is a continuation of U.S. application Ser. No. 16/466,478, filed on Jun. 4, 2019 and now issued as U.S. Pat. No. 11,357,920, which is the national stage entry of International Patent Application No. PCT/EP2017/081490, filed on Dec. 5, 2017, and claims priority to Application No. EP 16306633.5, filed on Dec. 7, 2016, the disclosures of which are incorporated herein by reference.

TECHNICAL FIELD

The present disclosure relates to a data collection device for attachment to an injection device and being configured for collecting medicament dosage information therefrom. The disclosure further relates to an injection system comprising an injection device and comprising a data collection device for attachment to the injection device.

BACKGROUND

A variety of diseases exists that require regular treatment by injection of a medicament. Such injections can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way injection needles that are replaced before each use. The insulin dose to be injected can then for instance be manually set or selected at the insulin pen by turning (dialling) a dial member and observing the actual dose from a dose window or display of the insulin pen. The dose is then injected by inserting the needle into a suited skin portion and pressing a trigger of the insulin pen, wherein the trigger may comprise an injection button.

To be able to monitor insulin injection, for instance to prevent false handling of the insulin pen or to keep track of the doses already applied, it is desirable to measure and capture information related to a condition and/or use of the injection device, such as for instance information on the injected insulin type and dose.

With some injection devices, such as the SoloSTAR device, e.g. described in WO2004/078239 A1, WO2004/078240 A1 or WO2004/078241 A1 a user has to set a dose of variable size by rotating a dose dial and a dose dial sleeve in a clockwise or dose-incrementing direction relative to a body or housing of the injection device. During such a rotation the dose dial and the dose dial sleeve move along a longitudinal and proximal direction relative to the housing because of a threaded engagement with the housing. For injecting and expelling of a dose of a liquid medicament the user will then have to depress a trigger or dose button in a distal direction and hence towards the body or housing of the injection device. Typically, the user uses his thumb for exerting a distally directed pressure onto the dose button, which is located at a proximal end of the dose dial and the dose dial sleeve, while holding the housing of the injection device with the remaining fingers of the same hand.

In order to equip such a mechanically operated injection device with a data collection device one has to bear in mind, that the displacement of the dose dial sleeve and of the dose dial relative to the housing of the injection device towards a proximal direction is somehow limited by the size of the hand of a user.

SUMMARY

In some embodiments of the present disclosure, the data collection device is advantageously rather compact and limited in its geometric size.

In certain embodiments, the data collection device provides a robust and reliable collection of dosage-related information even if the process of setting and expelling of a dose of a medicament is carried out by a user making use of both hands.

According to one aspect of the present disclosure's embodiments, a data collection device is provided for attachment to an injection device. The injection device comprises a trigger and a dial member as well as an expelling mechanism. During expelling of a medicament there occurs a relative rotation between the dial member and the trigger according to an advancing motion of the expelling mechanism or a component thereof. The trigger of the injection device is torque supportive coupled by friction and/or keeping to a housing of the injection device.

The data collection device comprises a body configured for attachment to the dial member, wherein during expelling of a medicament. The data collection device further comprises a sensor arrangement comprising at least a sensor arranged in or on the body. The sensor is configured to detect a rotation of the body relative to the trigger. The data collection device also comprises a processor arrangement configured to determine, based on the detected rotation, an amount of the medicament expelled by the injection device.

The data collection device is particularly configured for injection devices comprising a dial member rotatable relative to a trigger at least during the process of expelling or injecting of a dose of the medicament while the trigger, e.g. in the form of a dose button, is rotationally locked to a housing of the injection device. The body of the data collection device is fastenable or attachable to the dial member of the injection device. The body is rotationally lockable to the dial member. In this way the body rotates in unison and together with the dial member at least during dispensing or expelling of a dose of the medicament. Since the sensor arrangement is arranged in or on the body of the data collection device and since the trigger is rotationally locked to the housing of the injection device the sensor arrangement is particularly configured to detect a rotation of the body relative to the trigger.

The sensor arrangement is further configured to measure the rotation of the body relative to the trigger quantitatively. The processor arrangement is configured to process electrical signals obtained from the sensor arrangement in order to determine a degree of rotation of the body and hence of the dial member relative to the trigger and hence relative to the housing of the injection device during dispensing or expelling of a dose of the medicament. The number of revolutions of the body relative to the trigger and the degree of rotation of the dial member relative to the trigger during a dose expelling action is a direct measure for the quantity of the medicament expelled from the injection device. By detecting and quantitatively measuring the degree of rotation of the body of the data collection device relative to the trigger of the injection device the processor arrangement is configured to determine and to calculate an amount of medicament expelled by the injection device.

By measuring a degree of rotation of the dial member relative to the trigger of the injection device a rather compact and space saving design for the data collection device can be provided. The data collection device may comprise a rather compact geometric design such that when attached to the dial member the data collection device does not protrude in proximal direction from the proximal end of the injection device or from the trigger of the injection device. Due to a compact and miniaturized geometric design the data collection device may become rather attractive for end consumers and the data collection device may reach a comparatively high degree of user acceptance and user satisfaction.

The term "torque supportive coupled" expresses that the trigger is rotationally locked to the housing of the injection device as long as a torque acting on the trigger relative to the housing is below a given threshold. If the torque should exceed the threshold the trigger may be subject to a rotational movement relative to the housing without harming the integrity or functionality of the injection device. The term torque supportive coupled expresses that there might be a substantive limited rotational engagement between the trigger and the housing of the injection device. In some embodiments there may be even provided a rotational interlock between the trigger and the housing of the injection device.

The term "advancing of the expelling mechanism" relates to a dose expelling action conducted by the expelling mechanism or drive mechanism of the injection device. In typical embodiment the expelling mechanism or drive mechanism comprises a plunger or piston rod configured to get in axial abutment with a bung of a cartridge. During an expelling or dispensing action the plunger or piston rod is advanced in distal direction, i.e. towards a dispensing end of the injection device thereby urging the bung of the cartridge accordingly in distal direction, so as to expel a predefined amount of the medicament from the cartridge. The expelling mechanism or leads some components thereof may remain stationary during a dose expelling procedure. Some components of the expelling mechanism may be axially fixed or axially constrained in the housing of the injection device.

In another example the sensor arrangement of the data collection device comprises a sensor and a scale. One of the sensor and the scale is arranged in or on the body of the data collection device and the other one of the sensor and the scale is located on the trigger or is rotationally lockable to the trigger. In fact, the sensor is configured to detect a rotation relative to the scale. Since the trigger is rotationally locked to the housing of the injection device and since the body of the data collection device is connectable to the dial member, the sensor is configured to detect a rotation of the body relative to the trigger. Based on the detected rotation the processor arrangement is configured to determine an amount of the medicament expelled by the injection device. The scale may comprise a one or two-dimensional encoding along a sense of rotation relative to the sensor. The encoding is detectable by the sensor as the scale is subject to a rotation relative to the sensor.

In one example the sensor is located in or on a portion of the data collection device that rotationally locks to the trigger. In this way, the sensor is impeded to rotate during the expelling of the medicament while the scale is subject to a rotation relative to the sensor. Here, the scale may be rotationally locked to the dial member of the injection device when the data collection device is appropriately attached to the dial member. The scale may be rotationally engaged with the body of the data collection device while the sensor may be free to rotate relative to the body of the data collection device.

In another example the scale is rotationally lockable to the trigger while the sensor is attached or arranged to the body of the data collection device and wherein the sensor is rotationally locked to the body. Here, the scale may be impeded to rotate during expelling of the medicament while the sensor might be subject to a rotation.

With any example the sensor and the scale are subject to a mutual relative rotation. This relative rotation is identical or equivalent to a rotation of the dial member relative to the trigger of the injection device.

In one embodiment the body of the data collection device comprises a fastening portion with a cylindrically shaped sidewall forming a hollow receptacle section of the body, wherein the hollow receptacle section is configured to receive the dial member. The cylindrically-shaped sidewall and the hollow receptacle portion formed by the cylindrically-shaped sidewall provide a straightforward and easy attachment of the data collection device to the dial member of the injection device. The inside of the cylindrically-shaped sidewall may be provided with a friction enhancing structure so as to provide a slip free or clamped mechanical engagement and fastening of the body of the data collection device and the dial member of the injection device.

According to another embodiment the sensor is arranged at an inside of the sidewall of the body of the data collection device. The sensor may be integrated or embedded into the sidewall of the body. The sensor may be attached to the sidewall of the body of the data collection device. The sensor may be arranged inside the receptacle section formed by the sidewall of the body. The sensor may be therefore protected against environmental influences. Moreover, the sensor may be non-visible from outside the data collection device. The arrangement of the sensor inside the receptacle is beneficial to protect the sensor against disturbances or interferences from outside the data collection device.

Furthermore, the sensor is aligned radially inwardly with regard to the sidewall. Alternatively the sensor may be aligned axially with regard to the sidewall or with regards to a tubular shape of the body of the data collection device.

By aligning the sensor radially inwardly the sensor can be arranged at an axial position that substantially overlaps with the trigger of the injection device. In this way, a rather compact design of the data collection device at least in axial direction can be provided. Typically, the sensor is oriented or directed radially inwardly. It may be configured to detect and to measure a rotation of the body and hence of the dial member relative to the trigger with regards to an outer surface of the trigger that is e.g. enclosed by the body of the data collection device, e.g. by the cylindrically-shaped sidewall thereof.

In addition, the sensor may be arranged at a predefined axial distance from the receptacle section. In this way the sensor can be arranged at an axial offset to the receptacle section and hence at an axial offset of the dial member when the data collection device is attached to the dial member of the injection device. Consequently, the receptacle section is void of the sensor and can be optimized for a reliable, slip free and secure fastening of the data collection device to the injection device.

Furthermore, the sensor arrangement comprises a scale located on the trigger or rotationally lockable to the trigger. The scale typically extends along an outer circumference of a sidewall of the trigger that faces towards the sensor of the sensor arrangement. With embodiments, wherein the sensor is aligned axially with regard to the sidewall the scale may be located on an axial end face of the trigger, e.g. on a proximal end face of the trigger. The scale may comprise a circular structure and may be located around a radial center of the trigger end face.

Typically, the scale comprises some code or some other kind of visual or haptic discernible structure along its outer circumference so that the sensor will be capable to quantitatively detect and to quantitatively measure a rotation of the sensor relative to the scale. The sensor and the scale mutually correspond. If the sensor is for instance configured as a light sensitive sensor, such as a photodiode, the scale will comprise a visually discernible code or the like visually discernible structure. The scale may also comprise a predefined roughness or a surface structure providing a well-defined reflection pattern when illuminated with light. It is conceivable that the sensor comprises a light source and a corresponding optical detector. Here, an optical signal reflected from the surface structure of the scale may be indicative of a movement of the scale relative to the sensor. Comparable to an optical computer mouse variations in a reflection pattern are indicative of the degree or magnitude of a relative displacement between the scale and the sensor.

In other embodiments the sensor may comprise a magnetic sensor. Then the scale comprises a magnetic code along a circumferential direction. In other embodiments the sensor is an electric sensor configured to measure varying electric conductivities or electric permeabilities of the scale when rotating relative to scale. Hence, the sensor arrangement may comprise one or more of an optical sensor, a magnetic sensor, a capacitive sensor and a mechanical sensor.

The scale may be configured as a part of the trigger and may then belong to the injection device. In other embodiments the scale belongs to a separate mechanical element attached to the body of the data collection device. It may then belong to the data collection device. Consequently, the sensor arrangement comprising the sensor and a corresponding scale may be completely located on or in the data collection device or the sensor arrangement might be completed upon attaching the data collection device to the injection device.

In further embodiments the data collection device comprises a switch to activate at least one of the sensor arrangement and the processor arrangement. By means of a switch, the data collection device, in particular at least one of the sensor arrangement and the processor arrangement can be activated or deactivated on demand. The switch may be integrated into the body of the data collection device. The switch may be configured to activate at least the processor arrangement during or simultaneous with exerting a distally directed driving force onto the trigger. By means of a switch the data collection device can be switched at least between two different states or modes of operation. By means of the switch the data collection device may be switched from a sleep mode or idle mode into an activated mode and vice versa. Also, once activated the data collection device may return into a sleep mode or into an idle mode either after completion of a dose expelling procedure or after lapse of a predetermined time interval during which neither the data collection device nor the injection device have been operated.

In a further embodiment the switch is integrated into the sensor arrangement and the processor arrangement. The scale is arranged on the trigger and the trigger is axially displaceable relative to the dose member and hence relative to the body of the data collection device for initiating a dispensing procedure. In an initial configuration or in a rest position the scale of the trigger may be located axially offset from the axial position of the sensor. It may be only and due to an axial displacement of the trigger that the scale gets into a detection area of the sensor. Such an axial displacement of the trigger may be equally sensed and detected by the sensor. The sensor may be configured to detect and to quantitatively measure an axial displacement of the trigger relative to the dial member. An axial movement of the trigger relative to the sensor may be hence detected by the sensor. Then, a respective electrical signal may be transmitted to the processor arrangement thereby activating the processor arrangement and the sensor to quantitatively measure a rotation of the sensor relative to the trigger. In this way the function of a switch may be entirely integrated into the sensor arrangement and the processor arrangement. A separate switch may then become substantially superfluous.

The capability of the sensor arrangement to measure or to detect an axial displacement of the trigger relative to the dial member may be also used for detecting situations in which the rotational interlock of the trigger to the housing may be temporarily deactivated. An axial displacement of the trigger may be also a direct indication again of a rotational decoupling from the housing of the injection device. In this way and by measuring an axial displacement of the trigger an alert or a quantitative measurement can be provided that the injection device is not properly used.

In another embodiment the switch comprises a first switch component and a second switch component, wherein the first switch component is arranged on the body and wherein the second switch component is arrangeable in the housing or is attachable to the housing.

Additionally, the switch may comprise one of a mechanical switch, electric switch, magnetic switch or optical switch. By arranging two switch components on the body of the data collection device and in or on the housing of the injection device, respectively a movement of the body of the data collection device relative to the housing of the injection device can be detected. Alternatively, the switch and its switch components may be arranged only on or in the body of the data collection device. In other embodiments the switch may be configured to be of magnetic or capacitive type. The switch may be configured to activate the data collection device already at the beginning of a dose setting procedure, i.e. when a user starts to rotate the dial member of the injection device and hence when the user rotates the body of the data collection device relative to the housing of the injection device. In other words, the data collection device may be activated or switched on by means of the switch at the beginning of a dose dial procedure. The data collection device may then remain activated until the injection device returns into its initial configuration, i.e. in a zero dose configuration after termination of a dose expelling procedure.

Approaching or arriving in the initially configuration may be equally detected by the switch so as to deactivate at least one of the sensor arrangement and the processor arrangement. The switch may be configured to switch the data collection device from a sleep mode into an activated mode and vice versa from an activated mode into a sleep mode.

It is generally conceivable, that the data collection device is a one-piece device. Typically, the data collection device may be comprised of the body as the only mechanical component. A single piece or one-piece device is rather easy to handle and allows for a rather easy and straightforward attachment to the injection device. Moreover and since the data collection device is void of a plurality of mutually interacting and mutually displaceable mechanical components the data collection device can be rather robust. It may also provide a durable and long-lasting use.

In addition or alternatively the body comprises an axial through opening merging into the receptacle section, wherein the axial through opening is sized to receive the trigger when the body is attached to the dial member. By providing an axial through opening the body comprises a sleeve-like or collar-like shape. When attached to the injection device the fastening portion with the hollow receptacle section is oriented towards a distal direction, hence towards the injection end of the injection device. The axial through opening merging into the receptacle section is located at the opposite end, hence at a proximal end of the body of the data collection device. The axial through opening comprises an inner diameter or an inner cross-section that is at least slightly larger than an outer circumference or outer diameter of the trigger of the injection device.

In this way and when the data collection device is attached to the injection device the trigger of the injection device may extend axially through the axial through opening of the body of the data collection device. In this way, the trigger of the injection device is directly accessible by the user and it is directly depressible by the user of the injection device. The data collection device may therefore not interfere with the trigger or with the dose button of the injection device for initiating or for controlling a dose expelling procedure. Since the data collection device does not mechanically obstruct the trigger or since the data collection device avoids mechanical interference with the trigger the handling of the injection device at least in terms of expelling or injecting of a dose is not affected by the data collection device when attached to the injection device. In this way the overall attractiveness and a user's tendency to attach the data collection device to the injection device can be enhanced and improved.

In another embodiment the data collection device comprises a button attached to the body, wherein the button is axially displaceable relative to the body and wherein the button is freely rotatable relative to the body. By means of the button the trigger of the injection device may be covered when the data collection device is attached to the injection device. Typically, the button is provided instead of an axial through opening on the body so as to engage with the trigger of the injection device when the user intends to initiate a dose dispensing or dose expelling procedure. The button of the data collection device may provide or may coincide with a proximal end of the data collection device. The button may be axially slidably displaceable relative to the body. The button may be attached to the body so that the button is axially displaceable relative to the body within predefined axial margins. Since the button is freely rotatable relative to the body the button may rotationally lock to the trigger of the injection device while the body, which is rotationally lockable to the dial member, may rotate with the dial member of the injection device during a dose dispensing or dose expelling procedure.

Typically, the button of the data collection device is directly depressible by a user so as to advance the button relative to the body of the data collection device in a distal direction.

Typically, the button of the data collection device is mechanically engageable with the trigger of the injection device. Here, the button may be in a permanent axial abutment with the trigger of the injection device. A distally directed depression of the button of the data collection device may therefore directly transfer into a respective depression of the trigger relative to the housing of the injection device or relative to the dial member of the injection device.

Furthermore, the button may comprise an axially extending shaft with a tipped end section facing towards and getting in axial abutment with the trigger when the body is attached to the dial member. A tipped end section may be located in a radial center of the body of the data collection device. The tipped end section may comprise a spike and may be configured to axially engage with a radial center of a trigger end face. By means of the tipped end section the trigger may be displaced towards the distal direction when the button of the data collection device is depressed distally. For this the trigger end face may comprise a recess or an indentation again to receive the tipped end section. Since the mutual contact face between the tipped end section and the trigger end face is comparatively small, the trigger and the button are effectively rotationally decoupled from each other. Hence, the button may be subject to a rotation while the trigger and the trigger end face remains rotationally locked, rotationally fixed or at least torque supportive coupled to the housing of the injection device. The tipped end section of the button therefore rotationally decoupled the button of the data collection device from the trigger of the injection device.

According to another example the sensor is arranged on or in the button and the scale is arranged inside the body. In this way, the sensor and the scale can be concealed to the environment. They are hence invisible from outside the data collection device. The sensor may be located inside the button and may be directed towards the scale that is located in an interface section between the button and the body of the data collection device.

The scale may be rotationally locked to the body of the data collection device. The scale may rotate with the body of the data collection device as the body is rotated by a user in order to apply a torque to the dial member of the injection device. The button and the body of the data collection device are free to rotate relative to each other. The button may be subject to a limited axial displacement relative to the body. The button is axially engageable with the trigger of the injection device. When the data collection device is arranged and attached to the dial member the button may be in axial engagement with the trigger.

Depressing the button relative to the body may then lead to a corresponding depression, i.e. an axial displacement of the trigger relative to at least one of the dial member and the housing of the injection device. In this way, the button provides an axial force transmission element by way of which the trigger of the injection device is indirectly depressible. When the data collection device is arranged on the dial member the data collection device may entirely cover the trigger of the injection device. However, through the axial displacement of the button relative to the body the trigger is axially displaceable.

The button may comprise a hollow space thus forming a receptacle for the sensor and/or for the processor arrangement. The sensor and/or the processor arrangement may be encapsulated inside the button. The button may comprise a circular cross-section that is suitable to receive a button or coin battery so as to provide electric power to the sensor and/or to the processor arrangement.

The scale may be rotationally coupled to the body by means of a form fitting engagement with an inside section of a sidewall of the body. Such a mechanical coupling might be beneficial for an axial alignment with regards to the sensor. As the scale is subject to a rotation the sensor non-rotationally connected to the trigger or housing pointing in axial direction is configured to detect a varying encoding on the surface of the scale.

According to another example the scale comprises a scale disc having at least one radial protrusion or radial recess engaged and rotationally locked with a correspondingly-shaped radial protrusion or radial recess on an inside of the body. The scale disc may comprise a plastic disc or metal disc featuring a desired reflectivity for e.g. an optical sensor. Alternatively, the scale disc may comprise a magnetic encoding while the sensor is configured to detect a magnetization of portions of the scale disc. By means of mutually corresponding radial protrusions or radial recesses on an outside edge of the scale and on the inside of a sidewall of the body a torque-proof mechanical engagement between the scale disc and the body can be provided. The scale disc and the body are hence rotationally locked.

A rotation of the body relative to the trigger is unalterably transferred to a respective rotation of the scale disc. It is of particular benefit, when the scale disc comprises numerous radial recesses or radial protrusions to engage with correspondingly-shaped protrusions and/or recesses on the inside of the body. In this way a torque applied to the body can be homogeneously distributed among numerous pairs of radial protrusions and recesses around the circumference of the scale disc.

According to another example the scale disc is axially engaged with the button, i.e. axially connected to the button. For this, the radial protrusion or recess on the inside of the body may comprise or form a slotted link with the at least one radial protrusion or radial recess of the scale disc. Hence, the scale disc and the body may be in a sliding engagement in longitudinal or axial direction. For instance, an inside of the sidewall of the body comprises one or numerous axially extending ribs engaged with correspondingly-shaped recesses on an outer edge of the scale disc. In this way the scale disc can be displaced in axial direction relative to the body while it remains rotationally fixed and in torque-proof engagement with the body of the data collection device.

An axial engagement of the scale disc to the button is of benefit when the sensor is located in or on the button. In this way the axial distance between the sensor and the scale disc remains constant even when the button should be axially displaced relative to the body. A constant axial distance between the scale disc and the body is beneficial for the operation of the sensor. The sensor may be for instance implemented as an optical reflection sensor comprising a light source and a light detector. Light emitted by the sensor may be reflected on a surface of the scale. When an axial distance between the scale disc and the sensor remains constant the general reflection behavior of the scale disc and hence of the scale remains constant as well and varying optical signals detectable by the optical detector are a direct indication for that the scale disc has been subject to a rotation relative to the sensor. Here, code patterns or scale patterns that distinguish in terms of an optical property alternately align with the sensor as the scale rotates relative to the sensor.

In addition to that the scale disc may be also axially engaged with the body. It may be slidable relative to the body in axial or longitudinal direction between a proximal end position and a distal end position. In this way, the scale disc may be operable to prevent a disassembly of the body and the button. By means of the scale disc the body and the button may remain assembled.

According to another example the scale disc comprises a through opening and the button comprises an axially extending socket section with a groove on an outside section to engage an inside edge of the through opening of the scale disc. A rim of the groove of the socket section may comprise an outer diameter that is somewhat larger than an inside diameter of the through opening of the scale disc. The socket section and the button may be formed of a resilient material. They may comprise an injection molded plastic material. The scale disc, e.g. made of a metal disc, may be clipped into the groove with the inside edge of the through opening. In this way the scale disc can be axially fixed to the button.

The axially extending or axially protruding socket section on the outside of the bottom section of the button comprises an annular-shaped groove to receive the inside edge of the annular-shaped through opening of the scale disc. In this way, an upside facing or proximally facing surface of the scale disc may be in abutment with a lower side or a distal facing surface of the bottom section as the inside edge of the through opening of the scale disc is in engagement with the groove of the button's socket section. In this way, the scale disc is even axially supported and stiffened by the bottom section of the button.

According to another example the button comprises a sidewall and a bottom section forming an interior space to accommodate at least one of the sensor and the processor arrangement. The bottom section may comprise a substantially closed flat-shaped circular bottom that is unitarily formed with a cylindrically-shaped sidewall of the button. There may be provided one or several through openings in the bottom section. There may be provided at least one through opening or a window in the bottom section for an unhindered line of sight for the sensor located inside the interior space. Optical signals transmitted and/or received by the sensor may thus propagate through the through opening substantially unattenuated.

The interior space may be covered by a top portion, thus forming a lid of the button. The top portion may comprise and provide an end face serving as a thrust receiving surface to become depressed by a thumb of a user in order to initiate a dose expelling operation of the injection device. The top portion may be in direct contact with the sidewall to transfer an applied thrust from the top portion to the sidewall.

According to a further example the button comprises at least one of a button stem and a torque transmission structure on an outside of the bottom section. By means of a button stem, e.g. axially protruding from an outside of the bottom section a radial centering of the button relative to the trigger of the injection device can be provided when the trigger comprises a corresponding button stem receptacle.

Moreover and with another example, the bottom section is provided with a torque transmission structure, e.g. in form of a protruding slot to engage with a correspondingly-shaped recessed slot on a proximal surface of the trigger. In this way the button can be arranged in a torque transmissive way to the trigger of the injection device when the body of the data collection device is correctly assembled and attached to the dial member.

Insofar, the trigger of the injection device may comprise a torque transmission counter-structure to engage with the torque transmission structure of the button. When the data collection device is appropriately assembled to the dial member the button is in torque-proof engagement with the trigger of the injection device. Since the trigger is hindered to rotate relative to the housing of the injection device during expelling of a dose of the medicament also the button is hindered to rotate relative to the housing of the injection device while the body of the data collection device rotates in unison with the dial member of the injection device. A relative rotation between the button and the body can be detected and quantitatively monitored by means of the sensor and the scale, wherein one of the sensor and the scale is arranged in or on the body and wherein the other one of the sensor and the scale is located on the trigger or is rotationally locked to the trigger. In particular, the scale is arranged in or on the body and is hence rotationally locked to the body whereas the sensor is rotationally locked to the trigger.

In another example the data collection device comprises a scale drum rotationally lockable to the trigger when the body is attached to the dial member. By means of the scale drum and by rotationally locking the scale drum to the trigger the scale drum can provide a scale on its outer circumference to communicate with the sensor of the sensor arrangement. A scale drum is of particular benefit when a sidewall of the trigger is not accessible to the sensor of the sensor arrangement.

According to another embodiment the scale is arranged on an outer circumference of the scale drum. The scale drum may be located axially offset from the trigger. This allows and enables an increased flexibility with regard to a positioning of the sensor. Typically, the scale of the scale drum and the sensor should be located in a common transverse plane, which transverse plane extends substantially perpendicular to the longitudinal axis, hence perpendicular to the axial direction of the injection device. By means of the scale drum and the scale provided on its outer circumference, the sensor can be positioned at a predefined axial offset from e.g. a proximal end of the trigger. The scale drum enables an axially non-overlapping arrangement of the sensor and the trigger when the data collection device is attached to the injection device.

In another embodiment the scale drum is connected to the button and the scale drum is freely rotatable relative to the button. Typically, the scale drum and the button are axially connected. The scale drum is axially locked to the button. Any axial displacement or movement of the button relative to the body is equally transferred to a respective axial displacement of the scale drum relative to the body. Typically, the scale drum is axially fixed to the button. When the data collection device is attached to the injection device and in particular when the receptacle section of the body of the data collection device receives the dial member the scale drum is axially sandwiched between the button and the trigger of the injection device. An axial load or a distally directed force effect acting on the button may be unalterably transferred through the scale drum onto the trigger and vice versa.

Since the scale drum is freely rotatable relative to the button, the scale drum is rotationally decoupled from the button of the data collection device. This enables a rotation of the button of the data collection device relative to the trigger. Since the scale drum is rotationally lockable to the trigger a rotation of the body relative to the trigger or relative to the body of the data collection device has no influence on the detection or measurement conducted by the sensor arrangement. A rotational decoupling of the scale drum and the button allows and supports a rotation of the button of the data collection device during a measurement procedure or during a dose expelling or dose dispensing procedure conducted by the injection device. This enables and supports a handling of the injection device with two hands. A rotation of the button of the data collection device relative to the trigger of the injection device is therefore tolerable and has no detrimental effect on the measurement or detection conducted by the sensor arrangement and/or the processor arrangement of the data collection device.

In a further embodiment the data collection device comprises a rotary bearing 270 rotationally connecting the scale drum to the button. By means of a rotary bearing the scale drum is axially fixed to the button and is freely rotatable relative to the button. The rotary bearing may comprise a ball bearing so as to keep potential friction losses at a negligible minimum.

In another embodiment the scale drum comprises a drum end face that faces towards the trigger and wherein the drum end face comprises a friction enhancing structure or comprises a friction enhancing finish. A friction enhancing finish may be provided by a roughened surface of the drum end face that provides a comparatively high degree of friction between the drum end face and a respective end face of the trigger of the injection device. By means of the friction enhancing structure the scale drum can be rotationally locked to the trigger. The friction enhancing structure may provide a slip free engagement with the trigger of the injection device.

In a further embodiment the friction enhancing structure comprises a friction pad. The friction pad may be elastically or plastically deformable. The friction pad may be provided with a friction enhancing finish. The friction pad may comprise an elastomeric or a polymer-based material exhibiting a predetermined adhesive friction or static friction so as to enable a rotary interlock of the scale drum with the trigger of the injection device when the data collection device is attached or mounted to the injection device.

In a further embodiment the friction enhancing structure comprises at least one spike. The at least one spike pierces the proximal surface of the trigger of the pen when the button is pressed in distal direction thereby rotationally interlocking or rotationally fixing the drum end face and the trigger. A resilient member may help releasing the rotational fixation when removing the pressure by separating the drum end face and the trigger from one another. The enhancing structure may comprise a plurality of spikes that are configured to be short, thin and rigid, such that when pressure is released the rotational fixation is also released. In this case no resilient member may be required to separate the drum end face from the trigger.

In another embodiment the button comprises a disc-shaped button end face and an elongated shaft rotationally supported in the body. The button end face may extend substantially perpendicular to the elongation of the elongated shaft. Hence, the button may comprise a somewhat T-shaped geometry. The button end face may be substantially even and flat-shaped. It may comprise an annular outer rim or collar. An inner radial center of the button end face may be connected to the elongated shaft. The elongated shaft may be rotationally supported and axially displaceably arranged in a correspondingly-shaped axial bore or through opening of the body of the data collection device. The disc-shaped button end face may form a proximal end of the button and the elongated shaft thereof may extend towards the distal direction. The elongated shaft and the disc-shaped button end face may be integrally formed. The entire button may be manufactured as an injection molded plastic material.

In a further embodiment the rotary bearing is connected to an end section of the elongated shaft that faces away from the button end face. Typically, the rotary bearing may be radially widened relative to the elongated shaft. The radial extension of the rotary bearing is larger than a through opening of the bore through which the elongated shaft extends. By means of a radially widened rotary bearing and by means of the radially widened disc-shaped button end face the button is axially constrained to the body of the data collection device. Both, the disc-shaped button end face and the rotary bearing may provide and serve as an axial abutment with the body and may hence delimit an axial movement of the button relative to the body with regard to the proximal direction as well as with regard to the distal direction.

In another aspect there is provided a pen-type injection device for expelling of a number of user-selectable doses of a medicament. The injection device comprises an elongated housing extending along an axial direction and configured to accommodate a cartridge filled with the medicament and sealed by a bung that is displaceable in a distal direction for expelling of the medicament. The injection device also comprises a dial extension having a number sleeve helically coupled to the housing and further having a dial member and a trigger, wherein the dial member is configured to initiate or to control expelling of the medicament and wherein the dial member is arranged in a fixed rotational relationship to the number sleeve for allowing a user to move the dial extension to an extended position relative to the housing, wherein the extended position corresponds to the size of a dose deliverable by the injection device. The dial extension is pushable back to a rest position by depressing the trigger and the trigger is rotationally coupled to the housing by a torque transmission member that maintains the trigger member in a fixed angular relation relative to the housing.

The pen-type injection device is configured as a handheld injection device. A user may set a dose of the medicament by rotating the dial member in a dose incrementing direction thereby also rotating the number sleeve in the same direction, e.g. in a clockwise direction. Since the number sleeve is threadedly or helically coupled to the housing a rotation thereof leads to an axial displacement of the number sleeve and of the entire dial extension in a proximal direction relative to the housing. As the dial member and the number sleeve are rotated in the dose incrementing direction the dial extension continues to protrude and to extend beyond a proximal end of the housing. The magnitude of an axial displacement of the dial extension relative to the housing is directly proportional to the size of the dose of the medicament to be set and dispensed.

The trigger is typically arranged at a proximal end of the dial extension. The trigger may form a proximal end face of the dial extension. The trigger is axially displaceable relative to the number sleeve for switching the drive mechanism of the injection device from a dose setting mode into a dose dispensing mode. The trigger may be coupled to a clutch configured to switch the injection device between the dose setting mode and the dose dispensing mode. Upon depressing the trigger, e.g. in distal direction, the drive mechanism is switched into the dose dispensing mode. Due to a distally directed thrust or force effect acting on the trigger the number sleeve will start to rotate in an opposite direction, i.e. in a dose decrementing direction while the number sleeve and the dial extension return to the rest position.

In one embodiment the transmission member keeps the trigger in a fixed angular relation to the housing up to a torque of 0.005 Nm, 0.005 Nm, 0.010 Nm, 0.015 Nm, 0.020 Nm, 0.025 Nm or up to 0.030 Nm between the trigger and the housing. The transmission member provides the torque supportive coupling between the trigger and the housing of the injection device. A torque applied to the trigger above a threshold of 0.005 Nm, 0.010 Nm, 0.015 Nm, 0.020 Nm, 0.025 Nm or above 0.030 Nm may lead to a rotation of the trigger relative to the housing. Such a rotation would not harm the integrity or functionality of the injection device or of its expelling or drive mechanism. However, such a torque supportive coupling configured to prevent a rotation of the trigger relative to the housing as long as the torque applied to the trigger relative to the housing is below 0.005 Nm, 0.010 Nm, 0.015 Nm, 0.020 Nm, 0.025 Nm or below 0.030 Nm might be rather easy to implement in an injection device.

In a further embodiment the transmission member comprises a drive sleeve rotationally locked or rotationally lockable to the trigger. The drive sleeve may constitute the transmission member or may coincide with the transmission member. The transmission member and the drive sleeve may be permanently or selectively rotationally engageable with the housing and with the trigger. For instance and when the injection device is in a dose setting mode the drive sleeve may be rotatable relative to the housing. Then the drive sleeve may be rotationally locked to the number sleeve.

In another embodiment the transmission member is selectively rotationally lockable to the housing and the transmission member is rotationally locked to the number sleeve when the injection device is in a dose setting mode. The transmission member is rotationally locked to the housing and is slidably and axially displaceable relative to the housing when the injection device is in a dose dispensing mode.

As the drive mechanism is switched from the dose setting mode into the dose dispensing mode the clutch as operated by the trigger may interact with the transmission member or with the drive sleeve in such a way that the drive sleeve becomes rotationally locked to the housing and rotationally disengaged from the number sleeve. In the dose dispensing mode the drive sleeve is also axially displaceable relative to the housing. The trigger may be permanently or selectively rotationally locked or lockable to the drive sleeve. It is conceivable that the trigger rotationally locks to the drive sleeve as it is depressed for initiating the dose dispensing procedure. The transmission member prevents a rotation of the trigger relative to the housing during dose expelling. The position and orientation of the trigger may be therefore used as a reference for measuring a rotation of the dial member relative to the housing during dose dispensing. In the dose dispensing mode the drive sleeve is rotationally locked to the housing. It is rotationally decoupled from the number sleeve, which, during dose injection is subject to a helical motion relative to the housing.

In another aspect an injection system is provided comprising: an injection device and a data collection device as described above and being attachable to a dial member of the injection device. The injection device comprises an elongated housing extending along an axial direction (z) and configured to accommodate a cartridge filled with the medicament and sealed by a bung that is displaceable in a distal direction for expelling of the medicament. The injection device comprises a dial member rotatable relative to the housing during expelling of the medicament and a trigger displaceable in the axial direction relative to the dial member to initiate or to control expelling of the medicament, wherein the trigger is rotationally locked to the housing during expelling of the medicament.

The injection device typically comprises a drive mechanism that is controllable and configurable by means of the dial member and by means of the trigger. By means of the dial member, a dose of variable size can be set. Thereafter, by depressing the trigger the dose previously set can be dispensed or expelled from the cartridge. Typically, the dial member comprises an annular ring connected to a dose dial sleeve that is threadedly engaged with the housing of the injection device. During setting or dialing of a dose the dose dial sleeve is subject to a helical motion relative to the housing and is subject to a proximally-directed movement relative to the housing.

The dial member typically located at or near a proximal end of the dose dial sleeve is also subject to a proximally-directed displacement relative to the housing during setting of a dose. The trigger of the injection device is located at a proximal end of the dose dial sleeve. Depressing the trigger in a distal or dispensing direction leads to a switching of the injection device's drive mechanism from a dose setting mode into a dose dispensing or dose expelling mode. In response to a distally-directed force effect acting on the trigger the dose dial sleeve will rotate in an opposite, hence dose decrementing direction during which the dial member rotates in the same dose decrementing direction. The rotational motion of the dial member and the dose dial sleeve is accompanied by a respective movement of the dose dial sleeve and of the dial member in distal direction relative to the housing of the injection device.

During a dose setting and hence during a dose incrementing rotation of the dial member relative to the housing of the injection device the trigger may rotate in unison with the dial member. At least during dose dispensing the trigger is rotationally locked to the housing of the injection device while the dial member is subject to a dose decrementing rotation relative to the housing. Also during dose setting the trigger may be rotationally locked to the housing such that it is impeded from rotating relative to the housing.

During dose dispensing or dose expelling the body of the data collection device rotates with the dial member while the trigger of the injection device is rotationally locked to the housing of the injection device. Hence, the trigger is not subject to a rotation while the dial member and the body of the data collection member rotate relative to the housing and hence relative to the trigger of the injection device. It is then that the sensor arrangement is capable to quantitatively detect and to measure a degree of rotation of the body relative to the trigger. By means of the processor arrangement the degree of rotation of the dial member relative to the trigger and relative to the housing can be precisely determined. This is a direct indication or a direct measure for the size of the dose of the medicament actually dispensed or expelled from the cartridge.

In another example of the injection system the trigger comprises a trigger end face and at least one of a button stem receptacle and a torque transmission counter-structure on the trigger end face. The button stem receptacle is configured to receive a button stem of the data collection device, e.g. to receive a button stem of a button of the data collection device. The torque transmission counter-structure of the trigger is configured to engage with a complementary shaped torque transmission structure of the data collection device. For instance, the torque transmission counter-structure may comprise a recessed slot extending in radial direction across the trigger end face and the torque transmission structure comprises a correspondingly shaped protruding slot on a distal or lower face of the button of the data collection device. When assembled appropriately, the two mutually corresponding structures, hence the torque transmission structure and the torque transmission counter-structure, e.g. in form of the protruding slot and the recessed slot mutually engage in a torque transmitting way. In this way, the button of the data collection device is hindered to rotate relative to the trigger as the injection device is subject to a dose expelling procedure.

According to another example the trigger comprises a disc shaped trigger end face and a cylindrically-shaped trigger side wall, wherein the scale is located on the trigger side wall and wherein the scale extends along a circumference of the trigger side wall. In this way and by providing the scale on a cylindrically-shaped trigger sidewall the trigger of the injection device may extend axially through a correspondingly-shaped through opening of the body of the data collection device when the data collection device is attached to the injection device. The trigger of the injection device is still fully accessible to the user for operating the injection device. At the same time the rotation of the dial member relative to the trigger can be precisely measured by means of the data collection device. Since the data collection device may be axially intersected by a proximal end of the injection device when assembled thereto the overall axial extension of the injection system does not exceed and lies within the overall axial dimensions of the injection device. This allows for a rather direct and intuitive operation of the injection device even though the data collection device is attached thereto.

In addition or as an alternative the scale can be also provided on the trigger end face, e.g. at the proximal end face of the trigger. Such an embodiment enables alignment of the sensor along an axial or longitudinal direction with regards to the sidewall of the data collection device or with regards to the elongation of the pen-type injection device. The scale extends along a circular structure on the trigger end face. It may comprise a circle or a circular structure on the trigger end face and located at a radial distance from a radial center of the trigger end face. The sensor is positioned in a radial offset from the radial center of the trigger end face. It may be located at a predefined axial distance from the trigger end face and may be aligned along the axial direction.

In another embodiment of the injection system the injection device comprises a dial extension having a number sleeve threadedly engaged with the housing, wherein the dial member is arranged at a proximal end section of the dial extension and wherein the dial member is rotationally locked to the number sleeve.

The number sleeve may be permanently rotationally locked or connected to the dial member. A user-induced rotation of the dial member, e.g. in a dose incrementing direction, e.g. clockwise will lead to a corresponding rotation of the number sleeve. Typically, the number sleeve has a sequence of numbers provided or printed on its outer circumference. The sequence of numbers show up in a dose indicating window of the housing of the injection device as the number sleeve is subject to a rotation relative to the housing. The numbers are typically provided along a helix the pitch of which corresponding to the pitch of the threaded engagement of the number sleeve and the housing of the injection device. As the number sleeve is subject to a dose decrementing rotation relative to the housing during a dose dispensing or dose expelling procedure also the dial member rotates in the dose decrementing direction, e.g. counterclockwise.

In another embodiment the dial extension protrudes in a proximal direction from the elongated housing and wherein the dial extension moves in the proximal direction relative to the housing when the dial member is rotated in a dose incrementing direction.

In a further embodiment the number sleeve and the dial member rotate in a dose decrementing direction when the trigger is urged in the distal direction during or for expelling of the medicament. Furthermore, a cartridge and filled with the medicament is arranged inside the housing of the injection device. The housing of the injection device may comprise a main housing part or proximal housing part and a cartridge holder as a distal housing part. Hence, the housing of the injection device may comprise several components. The cartridge is typically accommodated in a distally located housing component, i.e. the cartridge holder whereas an expelling mechanism of the injection device, also denoted as drive mechanism, is typically accommodated and arranged inside the proximal housing component, i.e. the main housing part.

Typically, the drive mechanism of the injection device comprises at least a piston rod extending along the elongation of the housing of the injection device. The piston rod, typically comprising a radially widened pressure piece at a distal end is configured to operably engage with a piston of the cartridge so as to displace the piston in a distal direction, thereby expelling a dose of the medicament from the cartridge. With some injection devices the driving force for displacing the piston rod in distal direction is entirely provided by the user when depressing the trigger in distal direction. With other injection devices at least a portion of the driving force necessary for driving the piston rod in distal direction is provided by a mechanic or electric energy storage, such as a pre-tensed spring or by a battery configured for powering an electric drive.

In one embodiment a cartridge filled with the medicament is arranged inside of the housing of the injection device. Here, the injection device may be configured as a prefilled index again device with the cartridge readily assembled there in as the device is delivered to a user or patient.

In another embodiment the data collection device is attached to the dial member of the injection device. The data collection device may be permanently locked to the dial member of the injection device. The data collection device may be further detachably connectable to the dial member and hence to the injection device. The data collection device may be configured for attachment to a disposable injection device, which after one or several consecutive uses is intended to be discarded in its entirety. Before discarding of a disposable injection device the data collection device should be detached therefrom and should be attached to a new injection device. In this way the data collection device is configured to collect and to log medical dosage information of several injection devices. The medical dosage information gained by means of the data collection device is therefore independent of the specific injection device.

The term "drug" or "medicament", as used herein, means a pharmaceutical formulation containing at least one pharmaceutically active compound.

In one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010), H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the embodiments of the present disclosure without departing from the spirit and scope of the invention as it is defined by the claims. Further, it is to be noted, that any reference numerals used in the appended claims are not to be construed as limiting the scope of the invention.

BRIEF DESCRIPTION OF DRAWINGS

In the following various embodiments of a data collection device in connection with an injection device are described by making reference to the drawings, in which:

FIG. 13 shows an exploded view of the components of the data collection device, FIG. 14 is a perspective view of the button as seen from above, FIG. 15 is a perspective view of the button as seen from below.

DETAILED DESCRIPTION

Figure 1:
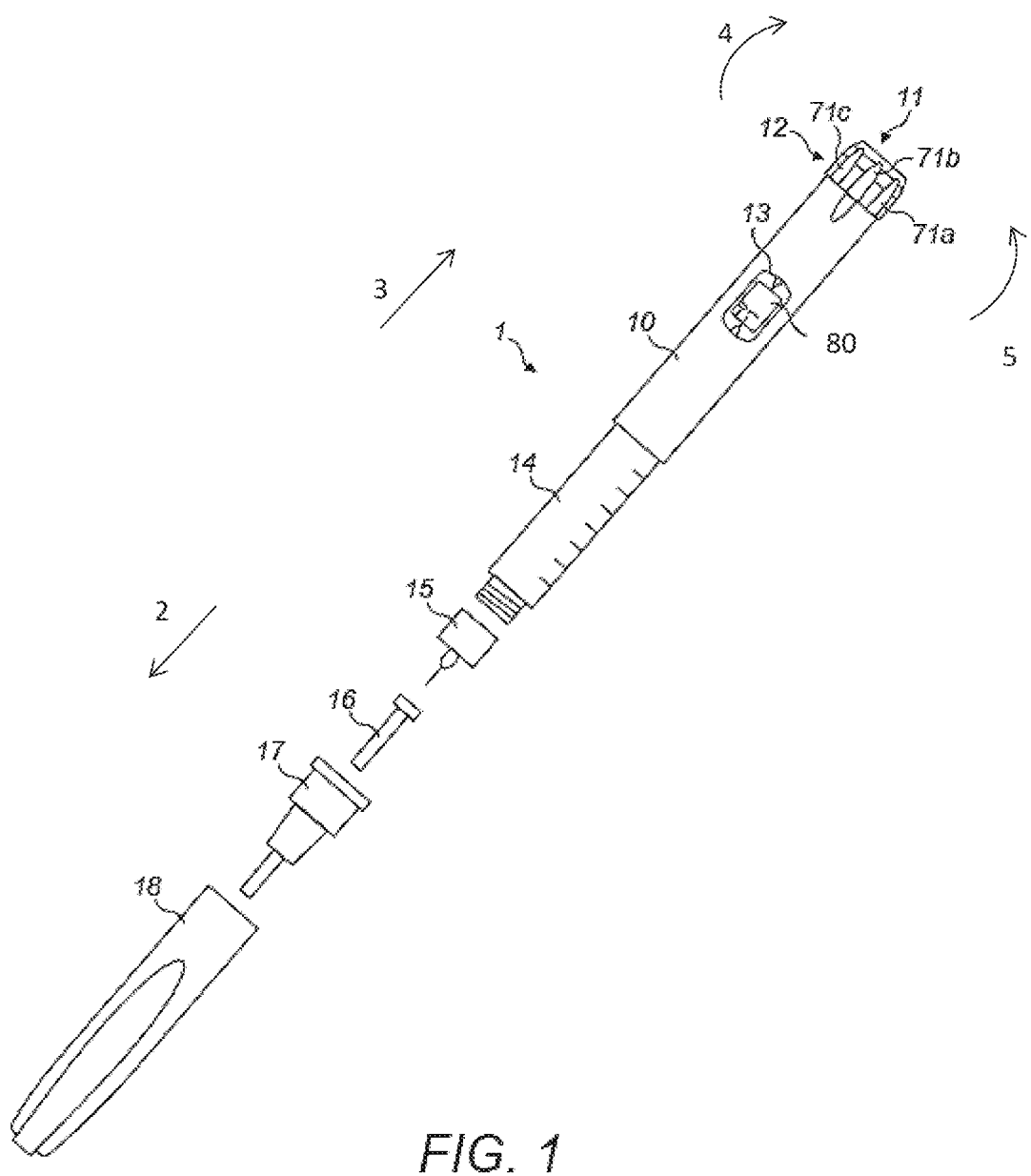
FIG. 1 shows an exploded view of an injection device for use with a data collection device according to an embodiment of the present disclosure.
Figure 8:
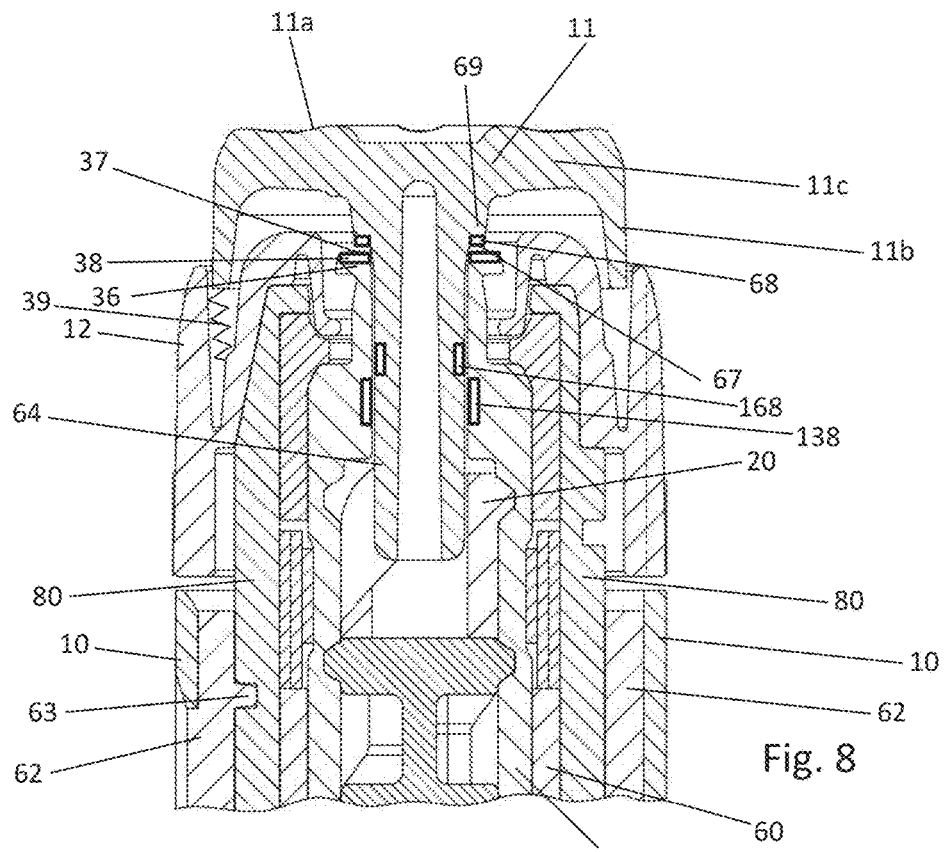
FIG. 8 is an enlarged cross-section through the proximal end of the injection device.
Figure 9:
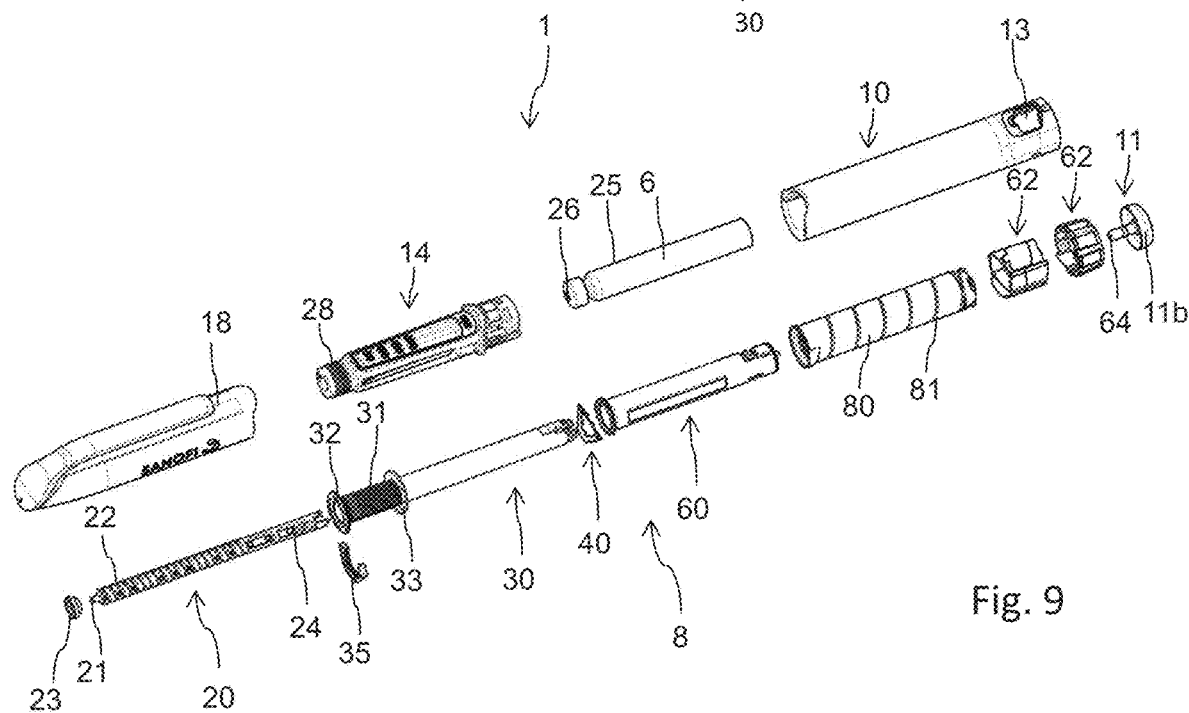
FIG. 9 is a further exploded view of the injection device as shown in FIG. 1.

The injection device 1 as shown in FIGS. 1 and 8 is a pre-filled disposable injection device that comprises a housing 10 to which an injection needle 15 can be affixed. The injection needle 15 is protected by an inner needle cap 16 and either an outer needle cap 17 or a protective cap 18 that is configured to enclose and to protect a distal section of the housing 10 of the injection device 1. The housing 10 may comprise and form a main housing part configured to accommodate a drive mechanism 8 as shown in FIG. 9. The injection device 1 may further comprise a distal housing component denoted as cartridge holder 14. The cartridge holder 14 may be permanently or releasably connected to the main housing 10. The cartridge holder 14 is typically configured to accommodate a cartridge 6 that is filled with a liquid medicament. The cartridge 6 comprises a cylindrically-shaped or tubular-shaped barrel 25 sealed in proximal direction 3 by means of a bung 7 located inside the barrel 25. The bung 7 is displaceable relative to the barrel 25 of the cartridge 6 in a distal direction 2 by means of a piston rod 20. A distal end of the cartridge 6 is sealed by a pierceable seal 26 configured as a septum and being pierceable by a proximally directed tipped end of the injection needle 15. The cartridge holder 14 comprises a threaded socket 28 at its distal end to threadedly engage with a correspondingly threaded portion of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dial member 12 at a proximal end of the injection device 1 may be displayed in so-called international units (IU, wherein 1 IU is the biological equivalent of about 45.5 µg of pure crystalline insulin (1/22 mg).

As shown in greater detail in FIGS. 2, 4, 5 and 6 the housing 10 comprises a dosage window 13 that may be in the form of an aperture in the housing 10. The dosage window 13 permits a user to view a limited portion of a number sleeve 80 that is configured to move when the dial member 12 is turned, to provide a visual indication of a currently set dose. The dial member 12 is rotated on a helical path with respect to the housing 10 when turned during setting and/or dispensing or expelling of a dose. In the example as shown in FIG. 1, the dial member 12 includes one or more formations 71a, 71b, 71c to facilitate attachment of a data collection device 100, 200 to the injection device 1, and in particular to the dial member 12.

The injection device 1 may be configured so that turning the dosage knob 12 causes a mechanical click sound to provide acoustical feedback to a user. The number sleeve 80 mechanically interacts with a piston in the insulin cartridge 6. When the needle 15 is stuck into a skin portion of a patient, and when the trigger 11 or injection button is pushed, the insulin dose displayed in display window 13 will be ejected from injection device 1. When the needle 15 of the injection device 1 remains for a certain time in the skin portion after the trigger 11 is pushed, a high percentage of the dose is actually injected into the patient's body. Ejection of an insulin dose may also cause a mechanical click sound, which is however different from the sounds produced when using the dial member 12.

In this embodiment, during delivery of the insulin dose, the dial member 12 is turned to its initial position in an axial movement, that is to say without rotation, while the number sleeve 80 is rotated to return to its initial position, e.g. to display a dose of zero units.

The injection device 1 may be used for several injection processes until either the cartridge 6 is empty or the expiration date of the medicament in the injection device 1 (e.g. 28 days after the first use) is reached.

Furthermore, before using injection device 1 for the first time, it may be necessary to perform a so-called "prime shot" to remove air from the cartridge 6 and the needle 15, for instance by selecting two units of the medicament and pressing trigger 11 while holding the injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user.

Figure 2:
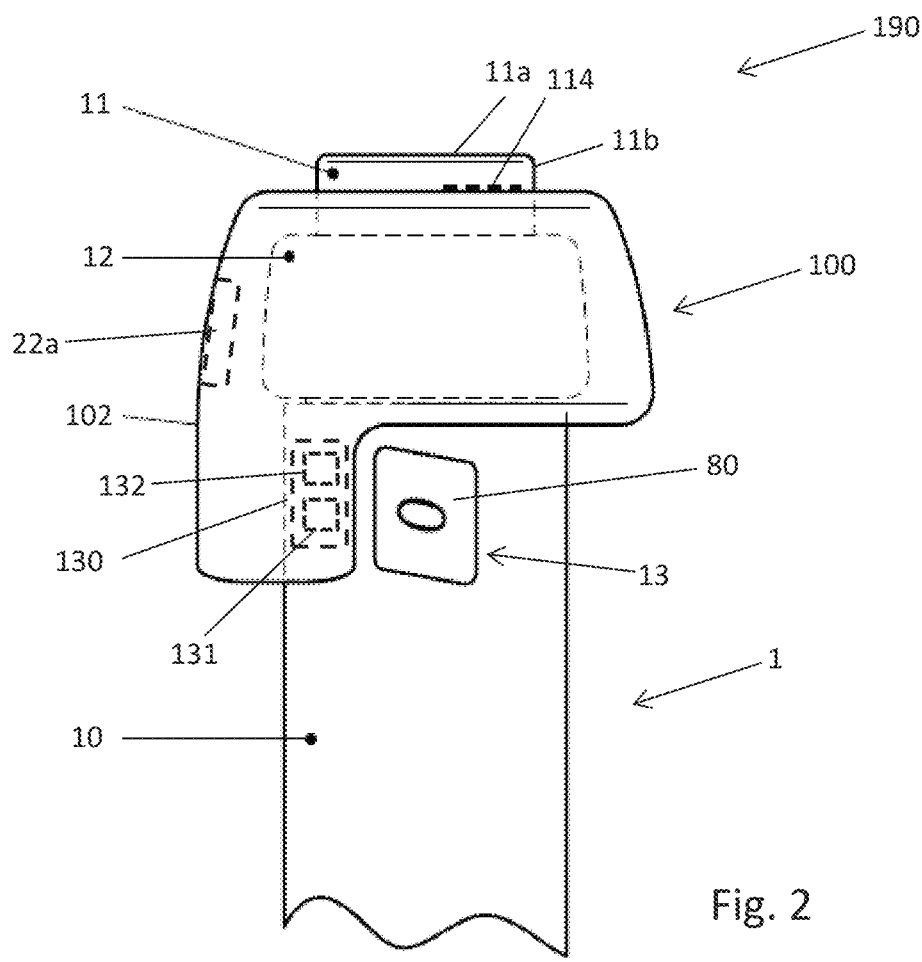
FIG. 2 is a schematic side view of a data collection device attached to a proximal end of the injection device.
Figure 4:
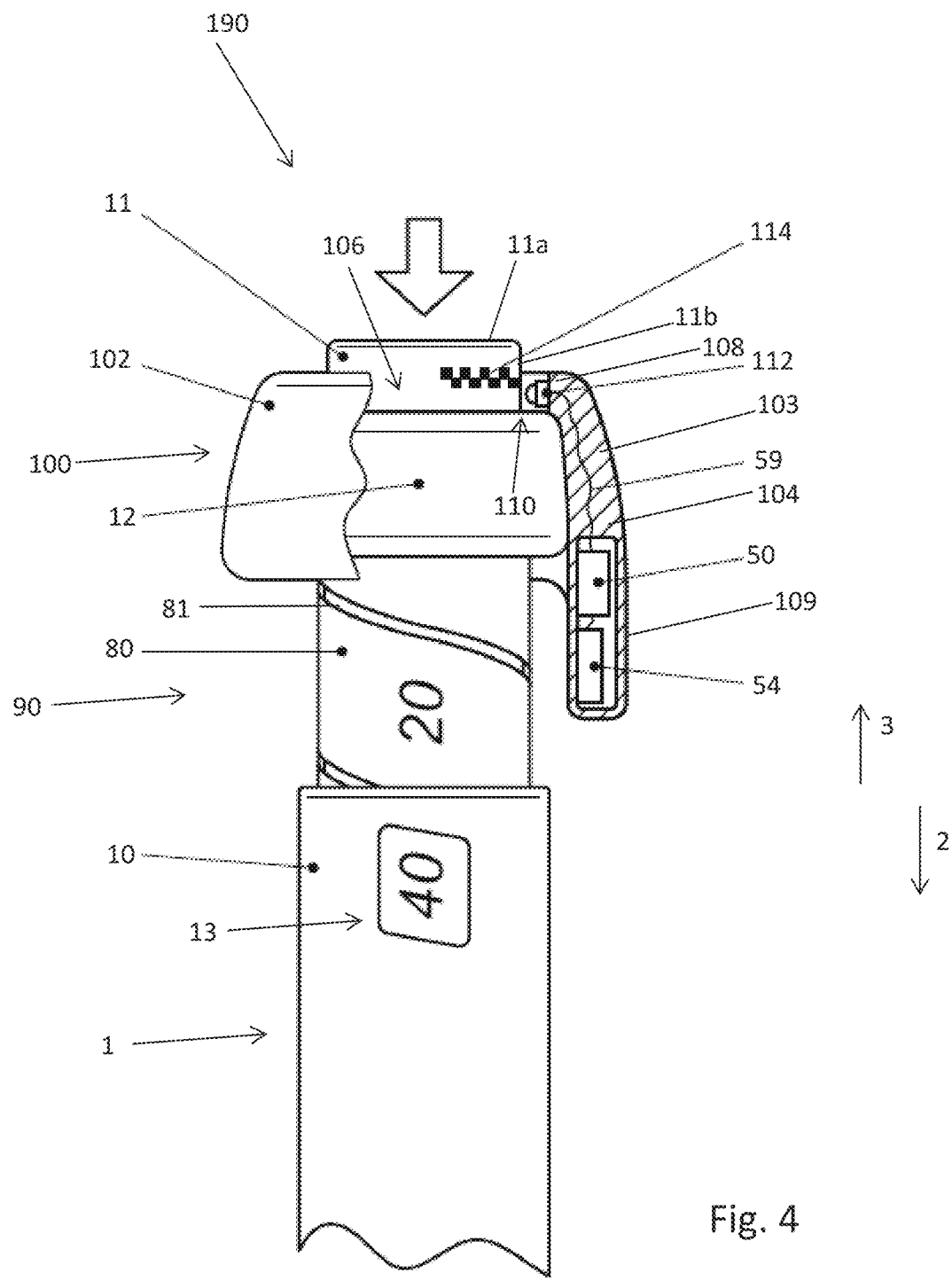
FIG. 4 is another view of the data collection device connected to the injection device according to FIG. 2 with the body of the data collection device partially cut away.

FIG. 2 is a side view of the proximal end of the injection device 1 when a data collection device 100 is attached. The data collection device 100 comprises a body 102. Inside the body and as shown in FIG. 4 there is provided a processor arrangement 50 and a power source 54. There is further provided a sensor arrangement 110 with a sensor 112 attached to or integrated into the body 102. As shown in FIG. 4, the sensor 112 is connected to the processor arrangement 50 by means of a wired connection 59. The wired connection 59 may be configured for transmission of electric energy to the sensor 112 as well as for transmission of electric signals from the sensor 112 to the processor arrangement 50. The body 102 comprises a fastening portion 103 that is configured to attach to the dial member 12 of the injection device 1. The body 102 may have the geometric form of a sleeve or of a collar to fit over the dial member 12. The body 102 and the fastening portion 103 form a hollow receptacle section 105 to receive the dial member 12 therein. The fastening portion 103 comprises a cylindrically-shaped sidewall 104. At an inside of the sidewall 104 there may be provided formations 107 as indicated in FIG. 4 to cooperate with the formations 71a, 71b, 71c on the dial member 12. With the mutually corresponding formations 107, 71a, 71b, 71c a rotational interlock can be provided between the body 102 and the dial member 12 when the data collection device 100 is attached to the injection device 1. The body 102 may be clamped to the dial member 12. It may be clipped to the dial member 12.

The formation 107 may also comprise some kind of a resilient padding of sufficient thickness to cooperate with the formations 71a, 71b, 71c on the dial member 12. The padding may be soft enough to conform to the surface of the dial member 12. It may be soft enough to conform to the formations 71a, 71b, 71c. A resilient padding may be further provided in addition to the formation or formations 107 on the inner surface of the sidewall 104. The resilient padding may deform to accommodate the dial member 12 within the receptacle section 105, hence within the cavity of the body 102. Friction provides a reactive force in response to insertion of the dial member 12 into the receptacle section 105. This provides tactile feedback to the user indicating that the data collection device 100 is being received over the dial member 12. Once the data collection device 100 is installed fully, a further axial movement is prevented. The friction between the data collection device 100 and the dial member 12 may cause the data collection device 100 to remain installed on the injection device 1. This can be achieved without any further fastening means or without any further mechanism. To uninstall the data collection device 100 from the injection device 1, the friction force needs to be overcome. This can be achieved by applying a comparatively strong pulling force, for instance of 30 N or more, to the data collection device 100 towards the proximal direction.

The padding and/or the formation 107 also provides sufficient engagement for transferring a rotation force applied by the user between the data collection device 100 and the dial member 12 during dose setting. The rotation force may be communicated by friction between the body 102 and the dial member 12. The friction force acting between the data collection device 100 and the dial member 12 in the rotational direction typically exceeds the force required to overcome the forces internal to the injection device 1 by a factor of at least 5, or more by a factor of at least 10, which helps to avoid slippage between these components.

Since the body 102 of the data collection device 100 entirely encloses the outer circumference of the dial member 12 it is actually the data collection device 100 and its body 102 that needs to be rotated, e.g. in a clockwise sense, hence in a dose incrementing direction 4 to set a dose prior to conduct an injection procedure. As the body 102 of the data collection device 100 is rotated by the user the dial member 12 will be subject to a corresponding rotation relative to the housing 10. During dose expelling or dose dispensing the user will have to depress the trigger 11 in the distal direction 2 so as to start and/or to control a dispensing operation. During dose dispensing the dial member 12 and hence the body 102 will rotate in the opposite dose decrementing direction 5, e.g. counterclockwise. Due to a slip free fastening and attachment of the body 102 to the dial member 12 the body 102 will rotate relative to the trigger 11 during the dose dispensing procedure since the trigger 11 is rotationally locked to the housing 10 at least during the process of dose dispensing or dose expelling.

Typically, a disc-shaped or flat-shaped trigger end face 11a of the trigger 11 is depressible by a thumb of a user in distal direction 2. As it is further shown in FIG. 4, the trigger 11 also comprises a trigger sidewall 11b of substantially cylindrical or annular shape. On the outer circumference of the trigger sidewall 11b there is provided a scale 114 to cooperate with the sensor 112 of the sensor arrangement 110. The scale 114 is encoded in circumferential or tangential direction, i.e. along the outer circumference of the trigger sidewall 11*b*. As the body 102 and the sensor 112 rigidly fastened to the body 102 start to rotate during dose dispensing relative to the trigger 11 the sensor 112 is configured to produce and to generate a sequence of electric sensor signals that correspond to the scale 114. The relative rotational movement of the sensor 112 and the scale 114 during dose dispensing is a direct measure of the degree of rotation of the body 102 relative to the housing 10. It is hence a direct indication and a direct measure for the size of a dose of the medicament dispensed or expelled from the cartridge 6.

Figure 3:
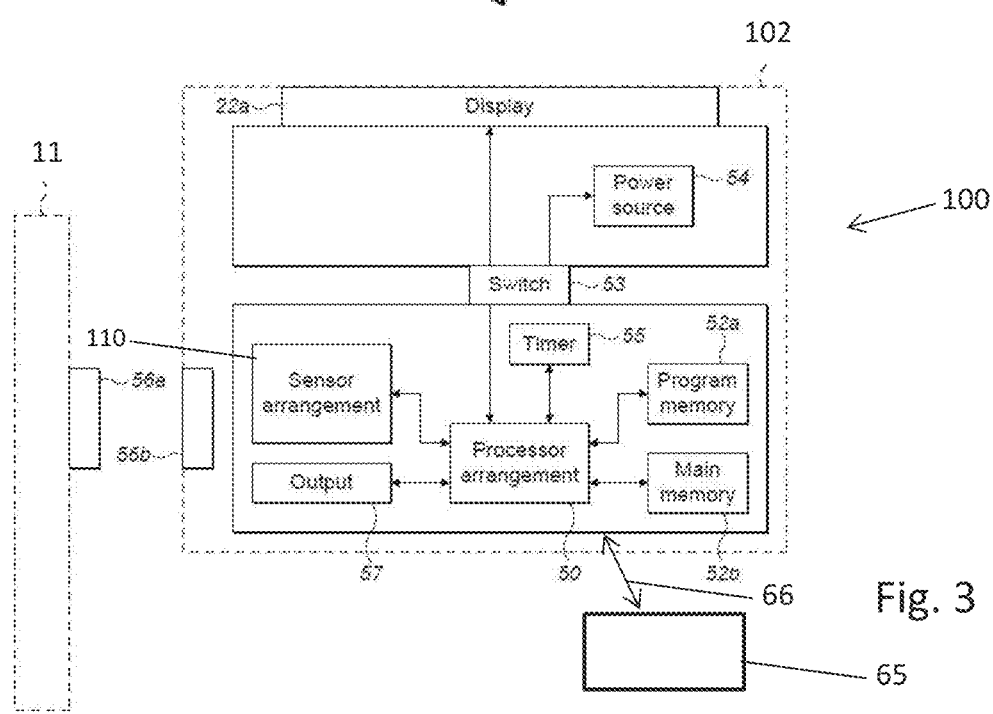
FIG. 3 is a schematic block diagram illustrating the various electric and electronic components of the data collection device.

In order to switch the injection device 1 from a dose setting mode as shown in FIGS. 3 and 4 into a dose injection or dose dispensing mode (not illustrated) the user has to depress the trigger 11 in distal direction 2 as indicated by the arrow in FIG. 4. The injection device 1 is then switched into the dose dispensing mode and the trigger 11 serving as a dose button is slightly displaced in distal direction 2 so that the scale 114 substantially aligns with the sensor 112 with regard to the axial direction. In the dose setting mode as shown in FIG. 4, the scale 114 is slightly axially offset from the position of the sensor 112. As indicated in FIG. 4, the sensor 112 is aligned radially inwardly. It is located at an inside of the sidewall 104 and points radially inwardly towards the outer circumference of the trigger 11. The trigger 11 of the injection device 1 axially extends through an axial through opening 106 of the body 102. The proximally located trigger end face 11*a* of the trigger 11 is located proximally from a proximal end of the body 102 of the data collection device 100.

The axial through opening 106 and the intersection of the data collection device 100 by the proximal end section of the injection device 1 provide a rather space saving arrangement of an injection system 190 that comprises the injection device 1 and the data collection device 100. Since the proximal end of the injection device and hence the trigger 11 reaches through the body 102 of the data collection device 100 the overall device handling of the injection device remains substantially unchanged and unaffected even when the data collection device 100 is attached to the dial member 12.

With the axial through opening 106 and with the trigger 11 axially extending through the through opening 106 a maximum dose to be set and dispensed with the help of the injection device 1 remains substantially unchanged compared to a configuration of the injection device without the data collection device 100. In particular the data collection device 100 does not prolong or increase the axial elongation of the injection device 1.

The dial member 12, the number sleeve 80 and the trigger 11 belong to a dial extension 90, which in its entirety axially separates from the housing 10 as a dose is set. During a dose dispensing action the entirety of the dial extension 90 returns towards the zero-dose configuration as shown in FIG. 2.

As illustrated in FIG. 4 the body 102 of the data collection device 100 comprises a radially inwardly extending flange portion 108 at its proximal end. The inner diameter or an inner cross-section in the region of the flange portion 108 is smaller than an outer diameter of the dial member 12. In this way, the flange portion 108 delimits or confines the receptacle section 105 of the body 102 in axial direction, in particular in the proximal direction 3. The radially inwardly extending flange portion 108 therefore serves as an axial stop to axially abut with a proximal end face of the dial member 12. When inserting the dial member 12 into the receptacle section 105 the radially inwardly extending flange portion 108 delimits a respective assembly motion. When reaching an abutment configuration as shown in FIG. 4 the sensor 112 is located at a predefined axial distance from the proximal end of the dial member 12 so as to properly align the sensor 112 with regard to the scale 114. The at least one sensor 112 is arranged on an inside of the flange portion 108. It may be also located elsewhere on the inside facing portion of the sidewall 104 as long as it faces towards the scale 114.

In order to activate or to wake up the electronic components of the data collection device 100 the data collection device 100 may be equipped with a switch 130 as indicated in FIG. 2. The switch 130 may comprise a first switch component 131 and a second switch component 132. The first switch component 131 is arranged on the body 102 of the data collection device 100 and the second switch component 132 is arrangeable in the housing 10 or it is attachable to the housing 10. The second switch component 132 may be readily assembled and provided in or on the housing 10 of the injection device 1. In a zero dose configuration it is conceivable that the first and the second switch components 131, 132 cooperate so as to close an electric switch. As soon as the body 102 is rotated relative to the housing 10, e.g. during setting of a dose, the first switch component 131 separates from the second switch component 132 thereby interrupting or opening the switch 130. This change in the switch configuration may be sensed or tracked by the processor arrangement 50 and/or may alter the electrical connection between the processor arrangement 50 and the power source 54.

A switching signal obtainable from the switch due to a relative displacement of the first and the second switch components may wake up the processor arrangement 50 and/or may wake up the sensor arrangement 110. As illustrated in FIGS. 2 and 4 the electronic components, namely the processor arrangement 50 and the power source 54 may be arranged inside an extension 109 of the body 102. Generally, the body 102 may comprise a cylindrical or collar-like shape that is substantially adapted to the overall geometry of the annular-shaped dial member 12. In order to provide sufficient space to accommodate the electronic components such as the processor arrangement 50 and the power source 54 the body 102 comprises a distally extending extension 109. In the extension 109 there may be also provided the switch 130.

In a zero-dose configuration as shown in FIG. 2 the extension 109 axially overlaps with the dosage window 13 but the extension 109 is located at a circumferential or tangential offset relative to the dosage window 13. In this way the dosage window 13 is not obstructed or covered by the extension 109. The axial elongation of the extension 109 is selected such, that it is located axially offset from the dosage window 13 after a complete revolution of the body 102 relative to the housing 10 in the course of setting of a dose. In this way an unobstructed appearance of the dosage window 13 is guaranteed for any conceivable constellation and position of the data collection device 100 relative to the housing 10.

Optionally and as indicated in FIG. 2 the data collection device 100 may be provided with a display 22*a* to visualize medical dosage information measured or gathered by the data collection device 100.

The first and second switch components 131, 132 may comprise electrical contacts that get in direct mutual mechanical contact in the zero-dose configuration. Alternatively it is conceivable, that the first and second switch components 131, 132 are implemented as capacitive sensors or as inductive sensors that provide a switch signal even without a direct mechanical contact there between.

FIG. 3 is a block diagram of the data collection device 100, 200. The data collection device 100, 200 includes a processor arrangement 50 including one or more processors, such as a microprocessor, a Digital Signal Processor (DSP), Application Specific Integrated Circuit (ASIC), Field Programmable Gate Array (FPGA) or the like, together with memory units 52a, 52b, including program memory 52a and main memory 52b, which can store software for execution by the processor arrangement 50 and data generated during use of the data collection device such as counted pulses, derived dose size, time stamp, etc. A switch 53 connects a power source 54 to the electronic components of the device, including the sensor arrangement 110, 210 when operated. The display 22a may or may not be present. The switch 53 maybe identical to the switch 130 or may coincide with the switch 130. The sensor arrangement 110 comprising one or more sensors, is provided for detecting rotational movement between the body 102 and the trigger 11.

The resolution of the sensor arrangement 110 is determined by the design of the injection device 1. A suitable angular resolution of the sensor arrangement 110 may be determined by Equation (1):

$$\text{resolution} = \frac{360°}{\text{units\_per\_rotation}} \quad (1)$$

For instance, if one full rotation of the dial member 12 corresponds to a medicament dosage amount of 24 IU, then a suitable resolution for the sensor arrangement 110 would be not more than 15°.

In the FIG. 2 embodiment, one or more first magnets 56a are provided around a circumference of the outer surface of trigger side all 11b and one or more second magnets 56b are provided around a circumference of sidewall 104 of the body 102. The sensor arrangement 110 can be implemented as a transducer that varies its output due to variations in the magnetic field, based on the Hall effect, as body 102 rotate relative to the trigger 11.

Since the body 102 rotates with the dial member 12 as the medicament is expelled from the injection device 1, the angle of rotation measured by the sensor arrangement 110 is proportional to the amount of medicament expelled. It is not necessary to determine a zero level or an absolute amount of medicament contained in the injection device 1. Moreover, since it is not necessary to monitor the numbers or tick marks on the number sleeve 80 displayed through the dosage window 13, the data collection device 100 may be designed so that it does not obscure the dosage window 13.

The medicament amount delivered is determined by the data collection device 100 independent from the dosage that is programmed into the injection device 1. Determining the delivered medicament amount provides a direct and thus more reliable information about the amount of medicament that is injected compared to data collection devices that determine the amount of medicament that is set, thus being intended to be dispensed.

However, in other embodiments, different types of sensor may be used. For example, instead of a transducer, the sensor arrangement may include a microelectromechanical (MEMS) device or other magnetic sensor for detecting changes in a magnetic field. Another example of an sensing arrangement is an optical encoder, including a light source, such as a light emitting diode (LED) and a light detector, such as an optical transducer, that monitors changes in light reflected from an inner surface of the first portion, where the inner surface first portion has one or regions of varying reflectivity around its circumference, such as tick marks or at least one shaped reflective region. Such a sensor arrangement is used in the second to fourth variations described above.

In other embodiments, the sensor arrangement 110 may be a potentiometer. In yet another embodiment, a capacitive sensing arrangement may be used, where elements provided on the trigger 11 may affect the capacitance between two plates in the sensor 112. In further examples, mechanical sensors, with mechanical switches and/or tracks, may be used to detect the relative rotation between the body 102 and the trigger 11.

While the embodiments described in detail includes only certain types of sensor in the sensor arrangement 110, other embodiments may be devised in which the sensor arrangement 110 includes multiple sensors of one or more types.

An output 57 of the processor arrangement 50 is provided, which may be a wireless communications interface for communicating with another device via a wireless network such as Wi-Fi or Bluetooth®, or an interface for a wired communications link, such as a socket for receiving a Universal Series Bus (USB), mini-USB or micro-USB connector. FIG. 3 depicts an example of an injection system 290 in which the data collection device 100 is connected to another external device 300, such as a personal computer 65, via a data connection 66 for data transfer. The data connection 66 may be of wired or wireless type. For example, the processor arrangement 50 may store determined delivered medicament amounts and time stamps for the injections as they are administered by the user and subsequently, transfer that stored data to the external electronic device 65. The device 65 maintains a treatment log and/or forwards treatment history information to a remote location, for instance, for review by a medical professional.

The data collection device 100 may be configured to store data such as delivered medicament amounts and time stamps of up to numerous injection events, such as 35 or more injection events. According to a once-daily injection therapy this would be sufficient to store a treatment history of about one month. Data storage is organized in a first-in first-out manner ensuring that most recent injection events are always present in the memory of the data collection device 100. Once transferred to an external electronic device 65 the injection event history in the data collection device 100 will be deleted. Alternatively, the data remains in the data collection device 100 and the oldest data is deleted automatically once new data is stored. This way the log in the data collection device is built up over time during usage and will always comprise the most recent injection events. Alternatively, other configuration could comprise a storage capacity of 70 (twice daily), 100 (three months) or any other suitable number of injection events depending on the therapy requirements and/or the preferences of the user.

In another embodiment, the output 57 may be configured to transmit information using a wireless communications link and/or the processor arrangement 50 may be configured to transmit such information to the external electronic device 65 periodically.

The processor arrangement 50 may control the optional display 22a to show the determined medicament dose information, and/or to show an elapsed time since a last medicament dose was delivered. For example, the processor arrangement 50 may cause the display 22a to switch periodically between displaying the most recent determined medicament dosage information and the elapsed time.

Figure 5:
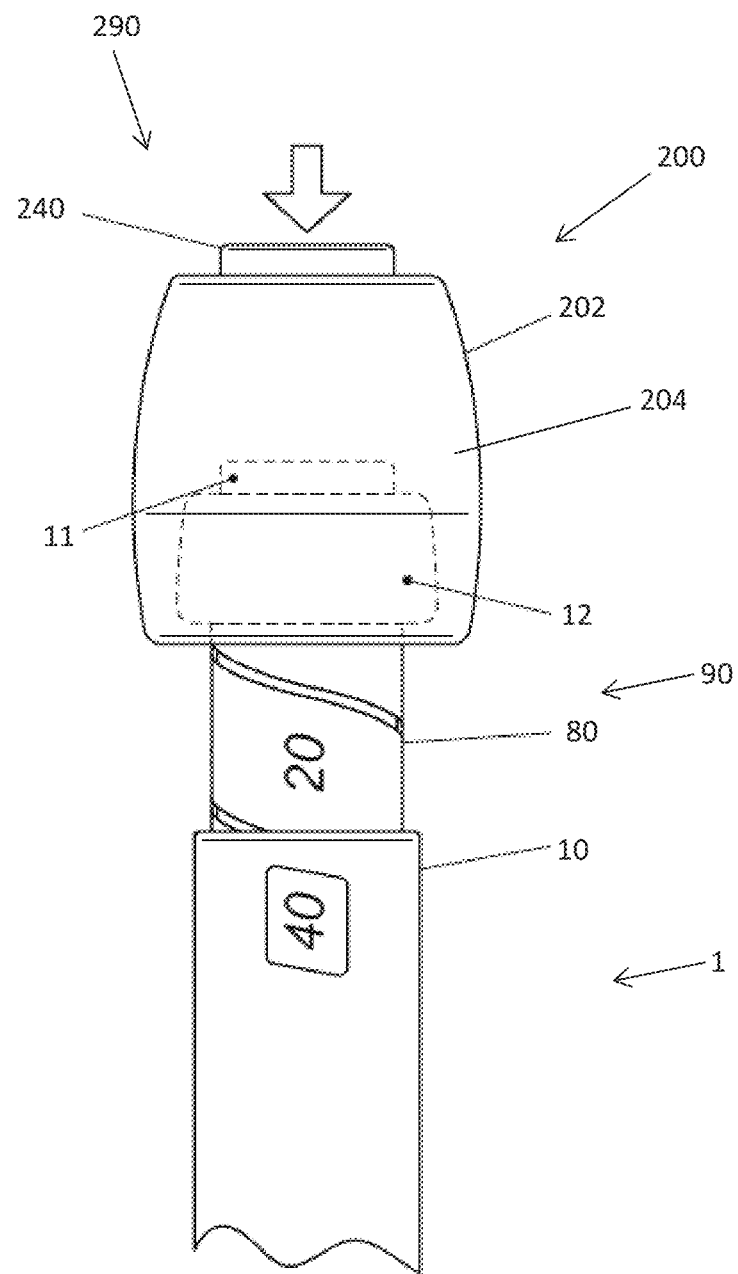
FIG. 5 is a side view of another embodiment of the data collection device attached to the injection device.
Figure 6:
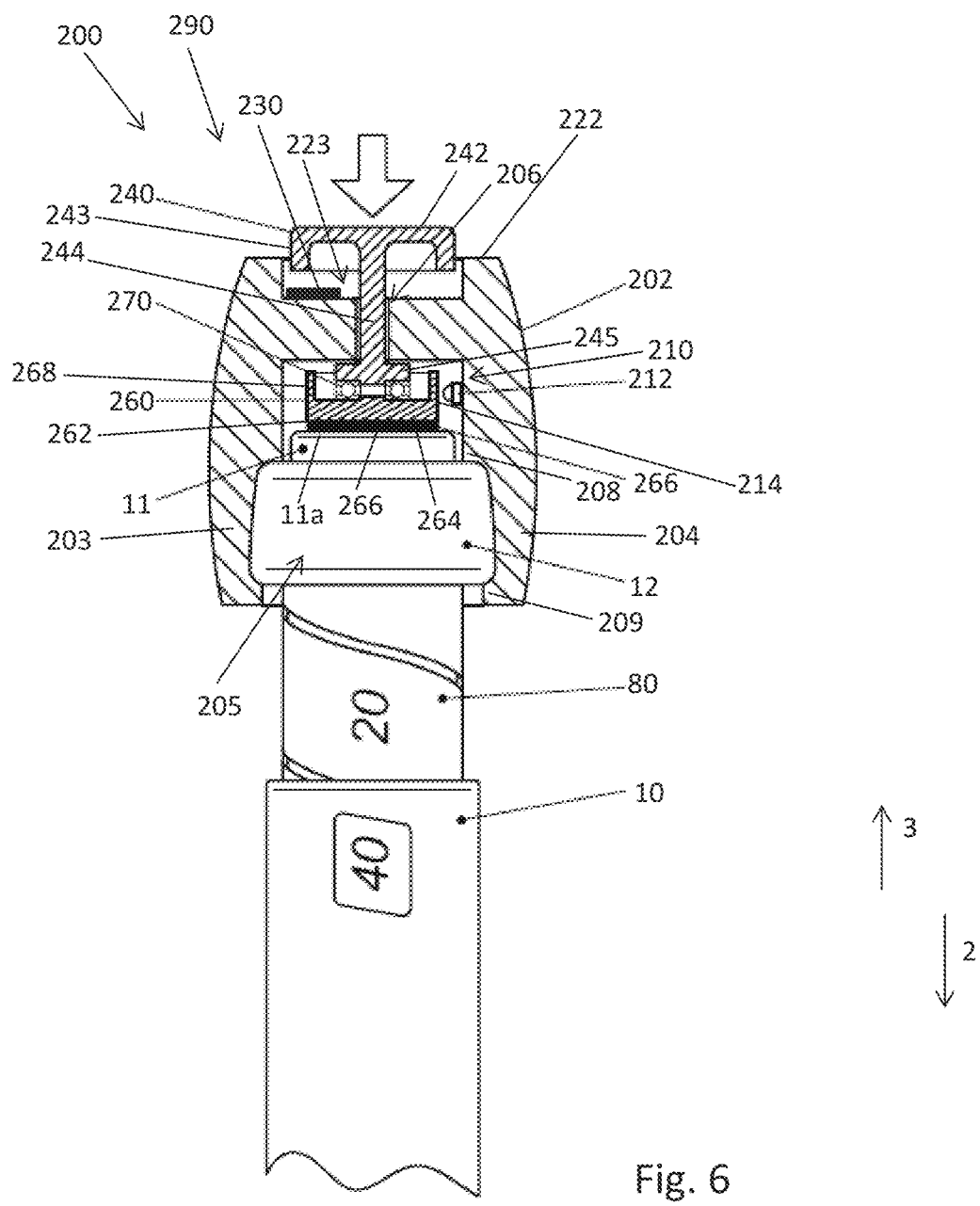
FIG. 6 is a cross-section through the data collection device according to FIG. 5.

The power source 54 may be a battery. The power source 54 may be a coin cell, or multiple coin cells arranged in series or parallel. In another embodiment as illustrated in FIGS. 5 and 6, the power source 54 may be a piezo-electric generator, which generates power when a button 240 of the data collection device 200 is pressed by the user, thereby potentially avoiding the need for a battery.

A timer 55 may be also provided. In addition to, or instead of, switching the data collection device 100 on and off, the switch 130 may be arranged to trigger the timer 55 when engaged and/or disengaged. For example, if the timer 55 is triggered on both engagement or disengagement of the first and second electrical contacts of the switch or both operation and ceasing of operation of the switch 130, then the processor arrangement 50 may use the output from the timer to determine a length of time during which the trigger 11 was pressed, for example to determine the duration of an injection.

Alternatively, or additionally, the processor arrangement 50 may use the timer 55 to monitor a length of time that has elapsed since an injection was completed, as indicated by a time of disengagement of the first and second switch components 131, 132 or ceasing of operation of the switch 130. Optionally, the elapsed time may be shown on the display 22a. Also optionally, when the first and second switch components 131, 132 are next engaged or when the switch 130 is next operated, the processor arrangement 50 may compare the elapsed time with a predetermined threshold, to determine whether a user may be attempting to administer another injection too soon after a previous injection and, if so, generate an alert such as an audible signal and/or a warning message on the display 22a. On the other hand, if the elapsed time is very short, it may indicate that the user is administering a medicament amount as a "split dose", and the processor arrangement 50 may store information indicating that a dosage was delivered in that manner. In such a scenario the elapsed time is compared with a predetermined threshold in the range of a few seconds, e.g. 10 seconds up to a few minutes, e.g. 5 minutes. According to an example the predetermined threshold is set to 2 minutes. If the time elapsed since the last injection is two minutes or less, the processor arrangement 50 stores information indicating that the dosage was delivered as a "split dose".

Another optional purpose for monitoring the elapsed time by the processor arrangement 50 is to determine when the elapsed time has passed a predetermined threshold, suggesting that the user might have forgotten to administer another injection and, if so, generate an alert.

In FIGS. 5 and 6 there is illustrated another embodiment of an injection system 290 comprising an injection device 1 and further comprising another data collection device 200 attached to a proximal end section of the injection device 1. Like the data collection device 100 as described in connection with FIGS. 2 and 4 the data collection device 200 also comprises a body 202 with a fastening portion 203 and a sidewall 204 to form a hollow receptacle section 205 configured to accommodate and to receive the dial member 12 of the injection device 1. Even though not illustrated in FIGS. 5 and 6 the data collection device 200 also comprises various electronic components, such as a processor arrangement 50 and a power source 54. In the same way as described above the inside facing sidewall portion of the sidewall 204 may comprise one or several formations 107 and/or a resilient padding, such as a foam rubber pad to enable a slip free attachment of the body 202 to the dial member 12.

The body 202 also comprises a radially inwardly extending flange portion 208 extending radially inwardly from the sidewall 204 and delimiting the fastening portion 203 and hence the receptacle section 205 in axial direction, in particular towards the proximal direction 3. At the opposite and distal end of the receptacle section 205 there is provided a further flange section 209 extending radially inwardly from the substantially cylindrically-shaped sidewall 204. The flange section 209 is a distal flange section 209 whereas the flange section 208 is a proximal flange section. The axial distance between the proximal flange section 208 and the distal flange section 209 substantially equals the axial dimensions of the dial member 12. The proximal flange section 208 acts and behaves as an axial end face to delimit an insertion motion of the dial member 12 into the receptacle section 205. As soon as an end of insertion configuration has been reached the distal flange section 209 clips over the distal end of the dial member 12. In this way, a kind of a clip connection between the body 202 and the dial member 12 is obtained. In this way, the dial member 12 and the body 202 are mutually fixed in axial direction as well as with regards to a circumferential direction.

Contrary to the embodiment of the data collection device 100 as shown in FIGS. 2 and 4 the data collection device 200 does not comprise an axial through opening that would be large enough to receive the trigger 11 therethrough. Instead the body 202 comprises a much smaller through opening 206 or bore that is large enough to receive a shaft 244 of a button 240 that is attached to the body 202 and which is axially displaceable relative to the body 202. The body 202 comprises a proximal end face 222 with a recess 223 in a radial central portion. The recess 223 is of somewhat cylindrical shape and is sized to receive a proximal end of the button 240. In the dose setting configuration as shown in FIGS. 5 and 6 the button 240, in particular the disc-shaped button end face 242 protrudes in proximal direction 3 from the end face 222 of the body 202. The button 240 is depressible in distal direction 2 so as to apply a corresponding distally directed pressure to the trigger 11 of the injection device 1. The button 240 comprises the disc-shaped button end face 242 having an annular collar 243 extending in distal direction. A radial central portion of the button end face 242 is connected or integrally formed with the shaft 244 extending through the correspondingly-shaped through opening 206 or bore of the body 202.

The through opening 206 extends into the interior of the hollow receptacle section 205. In the configuration as shown in FIG. 6 the distal end section 245 of the button 240 is radially enlarged or radially widened compared to the rod-shaped and axially extending shaft 244. In this way the radially widened end section 245 delimits a proximally directed displacement of the button 240 relative to the body 202. In the other direction the collar 243 delimits a distally directed displacement of the button 240 relative to the body 202, as the collar 243 axially abuts with a bottom of the recess 223. The shaft 244 and hence the entire button 240 is freely rotatable relative to the body 202.

At a distal end of the button 240 there is provided a scale drum 260. The scale drum is freely rotatable relative to the button 240. It is rotationally decoupled from the button 240. The button 240 is also rotationally decoupled from the body 202. The button 240 is axially displaceable relative to the body 202 within predefined axial margins. The distal end section 245 of the button 240 is axially fixed to the scale drum 260. The connection of the scale drum 260 and the button 240 is rigid in compression. A distally directed displacement of the button 240 relative to the body 202 equally transfers to a respective distally directed displacement of the scale drum 260. The scale drum 260 comprises a distally facing drum end face 262 that is provided with a friction enhancing structure 264 or with a friction pad 266. In this way and by means of the friction enhancing structure 264 and/or by means of the friction pad 266 the scale drum can be rotationally locked to the trigger 11.

Typically, the scale drum 260 comprises an annular or cylindrically-shaped sidewall 268 that is provided with a scale 214 to cooperate with the sensor 212 of the sensor arrangement 210. Like the sensor 112 also the sensor 212 is located at an inside facing portion of the receptacle 205. The sensor 212 is also aligned radially inwardly with regard to the sidewall 204.

There is further provided a rotary bearing 270 between the scale drum 260 and the distal end section 245 of the button 240. In other words, the rotary bearing 270 is axially sandwiched between the scale drum 260 and the button 240. By means of the rotary bearing, the scale drum 260 is axially fixed to the button 240 but is free to rotate relative to the button 240.

In FIG. 6 there is further schematically illustrated a switch 230 that is located on a bottom of the recess 223. As the button 240 is depressed in distal direction 2 the switch 230 may be depressed so as to activate the electronic components, hence at least one of the processor arrangement 50 and the sensor arrangement 210 of the data collection device. Here, the switch 230 may comprise a pressure sensitive switch or a pressure sensor. The switch 230 may be activated as the collar 243 of the button 240 gets in axial abutment with the switch 230.

Alternatively, the switch 230 may comprise a first switch component and the button 240 may comprise a second switch component, wherein the first and the second switch components may interact to generate a switching signal as the button 240 is moved relative to the body 202.

In order to detect and to measure a size of a dose actually dispensed by the injection device 1 the processor arrangement 50 and the sensor arrangement 210 are configured to detect and to measure a rotation of the body 202 relative to the scale drum 260. In operation it is intended that the scale drum 260 is rotationally locked or rotationally fastened to the trigger 11, which itself is rotationally locked to the housing 10 at least during a dose dispensing or dose expelling procedure. The body 202 and hence the sensor 212 rigidly fastened to the body 202 rotates in unison with the dial member 12 during dose dispensing. The scale drum 260 remains rotationally fixed to the trigger 11 and hence to the housing 10. In this way, the sensor 212 is configured to quantitatively measure the size of a dose as the sensor rotates around the outer circumference of the sidewall 268 of the scale drum 260. During and for initiating a dose dispensing procedure it is required that the user depresses the button 240 in distal direction 2 thereby exerting a pressure onto the trigger 11 that leads to a respective depression and distally directed displacement of the trigger 11 relative to the dial member 12.

Since the assembly of the button 240, the rotary bearing 270 and the scale drum 260 is rigid in compression, any distally directed force effect acting on the button 240 is directly and unalterably transferred to the trigger 11. In addition and due to the distally directed pressure acting on the button 240 a friction between the drum end face 262 an the trigger end face 11a is substantially increased so that any slip or any relative rotation between the trigger 11 and the scale drum 260 can be effectively prevented.

Under ordinary conditions of use the button 240 is depressed by a thumb of a user. Typically and in most cases the thumb of the user and hence the button 240 will not be subject to a rotation relative to the housing 10 of the injection device 1. However, there may be situations in which the button 240 experiences a rotation during a dose dispensing procedure, e.g. when the injection procedure is not conducted by one and a single hand but when the injection procedure is conducted with two different hands of a user. Then, the thumb or any other finger actually depressing the button 240 may twist or rotate relative to the housing 10. With the present embodiment such a rotation will not affect the measurement of a rotation of the scale drum 260 relative to the body 202 because the scale drum 260 is rotationally locked to the trigger 11 and the scale drum 260 is rotationally decoupled from the button 240.

The switch 130, 230 may be implemented as a mechanical switch. It is even conceivable that the switch 130, 230 is located elsewhere on the outer circumference of the body 102, 202 and that the switch 130, 230 is manually activated by the user prior to conduct a dispensing procedure.

The scale 114, 214 may be printed on the outer circumference of the trigger sidewall 11b or on the sidewall 268 of the scale drum 260. The scale 114, 214 may be also imprinted or engraved on the respective sidewall sections. It is even conceivable, that the scale comprises an immanent roughness with a predefined granulation or grid size and that the sensor 112, 212 does not only comprise a photodiode but also a light source, such as a Light Emitting Diode (LED). The LED may illuminate the scale 114, 214 and there may arise a speckle pattern with a well-defined structure or granularity allowing to quantitatively determine a degree of rotation as the speckle pattern moves when the scale 114, 214 is subject to a movement or rotation relative to the sensor 112, 212.

Figure 7:
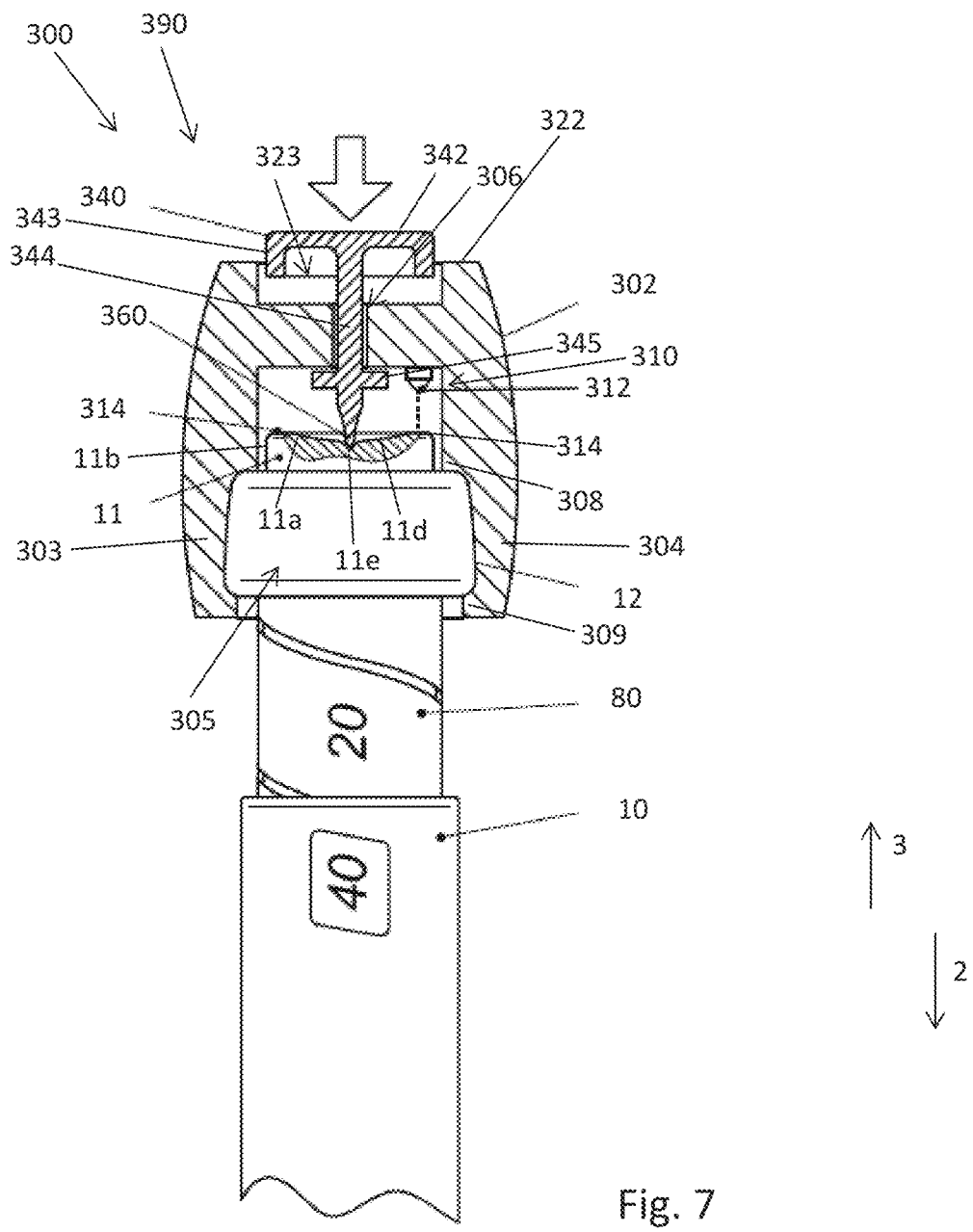
FIG. 7 is a cross-section through another embodiment of the data collection device.

In FIG. 7 there is further illustrated another embodiment of an injection system 390 comprising an injection device 1 and further comprising another data collection device 300 attached to a proximal end section of the injection device 1. Like the data collection device 300 as described in connection with FIGS. 5 and 6 the data collection device 300 also comprises a body 302 with a fastening portion 303 and a sidewall 304 to form a hollow receptacle section 305 configured to accommodate and to receive the dial member 12 of the injection device 1. Even though not illustrated in FIG. 7 the data collection device 300 also comprises various electronic components, such as a processor arrangement 50 and a power source 54. In the same way as described above the inside facing sidewall portion of the sidewall 304 may comprise one or several formations 107 and/or a resilient padding, such as a foam rubber pad to enable a slip free attachment of the body 302 to the dial member 12.

The body 302 also comprises a radially inwardly extending flange portion 308 extending radially inwardly from the sidewall 304 and delimiting the fastening portion 303 and hence the receptacle section 305 in axial direction, in particular towards the proximal direction 3. At the opposite and distal end of the receptacle section 305 there is provided a further flange section 309 extending radially inwardly from the substantially cylindrically-shaped sidewall 304. The flange section 309 is a distal flange section 309 whereas the flange section 308 is a proximal flange section. The axial distance between the proximal flange section 308 and the distal flange section 309 substantially equals the axial dimensions of the dial member 12. The proximal flange section 308 acts and behaves as an axial end face to delimit an insertion motion of the dial member 12 into the receptacle section 305. As soon as an end of insertion configuration has been reached the distal flange section 309 clips over the distal end of the dial member 12. In this way, a kind of a clip connection between the body 302 and the dial member 12 is obtained. In this way, the dial member 12 and the body 302 are mutually fixed in axial direction as well as with regards to a circumferential direction.

Like the body 202 of the data collection device 200 the body 302 of the data collection device 300 comprises through opening 306 or bore that is large enough to receive a shaft 344 of a button 340 that is attached to the body 302 and which is axially displaceable relative to the body 302. The body 302 comprises a proximal end face 322 with a recess 323 in a radial central portion. The recess 323 is of somewhat cylindrical shape and is sized to receive a proximal end of the button 340. In the dose setting configuration as shown in FIG. 7 the button 340, in particular the disc-shaped button end face 342 protrudes in proximal direction 3 from the end face 322 of the body 302. The button 340 is depressible in distal direction 2 so as to apply a corresponding distally directed pressure to the trigger 11 of the injection device 1.

The button 340 comprises the disc-shaped button end face 342 having an annular collar 343 extending in distal direction. A radial central portion of the button end face 342 is connected or is integrally formed with the shaft 344 extending through the correspondingly-shaped through opening 306 or bore of the body 302.

The through opening 306 extends into the interior of the hollow receptacle section 305. In the configuration as shown in FIG. 7 a portion of the shaft 244 located inside the receptacle section 305 comprises a flange portion 345 that is radially enlarged or radially widened compared to the rod-shaped and axially extending shaft 344. The radial dimension of the flange portion 345 is larger than the diameter of the through opening 306. In this way the flange portion 345 delimits a proximally directed displacement of the button 340 relative to the body 302. In the other direction the collar 343 delimits a distally directed displacement of the button 340 relative to the body 302, as the collar 343 axially abuts with a bottom of the recess 323. The shaft 344 and hence the entire button 340 is freely rotatable relative to the body 302.

The button 340 comprises a tipped end section 360 that is in axial abutment with the trigger end face 11a when the data collection device 300 is attached to the dial member 12. The tipped end section 360 forms a distal end of the button 340. It is located distally from the radially widened flange section 345. The distal and tipped end section 360 may comprise a spike having a rather small or almost negligible contact surface with the trigger end face 11a. For a secure, reliable and well-defined axial abutment of the button 340 and the trigger 11 the trigger end face 11a comprises an axial recess 11d to form a well-defined support for the end section 360. The trigger end face 11a may also comprise an axial indentation 11e with a geometric shape that communicates with the end section 360 of the button 340.

In the embodiment according to FIG. 7 the sensor arrangement 310 comprises a sensor 312 aligned in axial direction and further comprises a scale 314 provided on the trigger end face 11a. The scale 314 may comprise a code or another visually discernible structure extending along an imaginary circle on or near an outer edge of the trigger end face 11a. The scale 314 faces in proximal direction 3 and the sensor 312 is aligned and oriented towards the distal direction 2. Typically, the scale 314 is located at a regular distance from the radial center or from the indentation 11e the of the trigger end face 11a. Likewise, the sensor 312 is located at a radial offset from the center of the trigger end face 11a and at a given radial offset from the through opening 306 of the body 302. The sensor 312 is located at a distally facing end face of the body 302 axially confining or axially delimiting the receptacle section 305 of the body 302 towards the proximal direction 3.

Since the end section 360 of the button 340 engages with a radial center of the trigger end face 11a a distally directed thrust and a corresponding distally directed displacement of the button 340 leads to a respective distally directed movement of the trigger 11 relative to the dial member 12. As it is apparent from FIG. 7, there is provided at least a small gap between an inside facing sidewall section of the sidewall 304 and an outside facing side wall 11b of the trigger 11. In addition and due to the radial central abutment of the button 340 and the trigger 11 the trigger 11 will not experience a tilting motion when depressed in distal direction again. There might be also a gap between a proximal end face of the dial member 12 and the trigger sidewall 11b when the trigger 11 is depressed for expelling of a dose. In this way the trigger 11 may be in a contact-less configuration with regard to the body 302 and with regard to the dial member 12. When the dial member 12 rotates in unison with the body 302 of the data collection device 300 there will be substantially no friction between the trigger 11 and any one of the body 302 or the dial member 12. The distally directed thrust acting on the button 340 and the trigger 11 may bring the trigger 11 in frictional engagement with a further component of the drive- or expelling mechanism 8 of the injection device 1.

Since there is provided a rather tiny and almost negligible contact surface between the button 340 and the trigger 11 the button 340 is rotationally supported on the trigger 11. A friction force between the tipped end section 360 and the trigger 11 is almost negligible. In effect, and due to the tipped end section 360 the button 340 is effectively rotationally decoupled from the trigger 11 when the data collection device 300 is attached to the dial member 12. During a dose expelling procedure the button 340 may become subject to a rotation relative to the trigger 11.

Such a rotational movement would have no influence on the measurement conducted by the sensor arrangement 310.

The embodiment of the data collection device 300 as shown in FIG. 7 is void of a scale drum 260 compared to the embodiment of the data collection device 200 as shown in FIGS. 5 and 6. The device 300 according to FIG. 7 may therefore comprise a reduced axial extension compared to the device 200. The tipped end section 360 of the button 340 may be beneficial to limit the total number of components of the data collection device 300 and to reduce the overall dimensions thereof.

The expelling or drive mechanism 8 as shown in more detail in FIGS. 8 and 9 comprises numerous mechanically interacting components. A flange like support of the housing 10 comprises a threaded axial through opening threadedly engaged with a first thread or distal thread 22 of the piston rod 20. The distal end of the piston rod 20 comprises a bearing 21 on which a pressure foot 23 is free to rotate with the longitudinal axis of the piston rod 20 as an axis of rotation. The pressure foot 23 is configured to axially abut against a proximally facing thrust receiving face of the bung 7 of the cartridge 6. During a dispensing action the piston rod 20 rotates relative to the housing 10 thereby experiencing a distally directed advancing motion relative to the housing 10 and hence relative to the barrel 25 of the cartridge 6. As a consequence, the bung 7 of the cartridge 6 is displaced in distal direction 2 by a well-defined distance due to the threaded engagement of the piston rod 20 with the housing 10.

The piston rod 20 is further provided with a second thread 24 at its proximal end. The distal thread 22 and the proximal thread 24 are oppositely handed.

There is further provided a drive sleeve 30 having a hollow interior to receive the piston rod 20. The drive sleeve 30 comprises an inner thread threadedly engaged with the proximal thread 24 of the piston rod 20. Moreover, the drive sleeve 30 comprises an outer threaded section 31 at its distal end. The threaded section 31 is axially confined between a distal flange portion 32 and another flange portion 33 located at a predefined axial distance from the distal flange portion 32. Between the two flange portions 32, 33 there is provided a last dose limiting member 35 in form of a semi-circular nut having an internal thread mating the threaded section 31 of the drive sleeve 30.

The last dose limiting member 35 further comprises a radial recess or protrusion at its outer circumference to engage with a complementary-shaped recess or protrusion at an inside of the sidewall of the housing 10. In this way the last dose limiting member 35 is splined to the housing 10. A rotation of the drive sleeve 30 in a dose incrementing direction 4 or clockwise direction during consecutive dose setting procedures leads to an accumulative axial displacement of the last dose limiting member 35 relative to the drive sleeve 30. There is further provided an annular spring 40 that is in axial abutment with a proximally facing surface of the flange portion 33. Moreover, there is provided a tubular-shaped clutch member 60. At a first end the clutch member 60 is provided with a series of circumferentially directed saw teeth. Towards a second opposite end of the clutch member 60 there is located a radially inwardly directed flange.

Furthermore, there is provided a dose dial sleeve also denoted as number sleeve 80. The number sleeve 80 is provided outside of the spring 40 and the clutch member 60 and is located radially inward of the housing 10. A helical groove 81 is provided about an outer surface of the number sleeve 80. The housing 10 is provided with the dosage window 13 through which a part of the outer surface of the number 80 can be seen. The housing 10 is further provided with a helical rib at an inside sidewall portion of an insert piece 62, which helical rib 63 is to be seated in the helical groove 81 of the number sleeve 80. The tubular shaped insert piece 62 is inserted into the proximal end of the housing 10. It is rotationally and axially fixed to the housing 10. There are provided first and second stops on the housing 10 to limit a dose setting procedure during which the number sleeve 80 is rotated in a helical motion relative to the housing 10.

The dose member 12 in form of a dose dial grip is disposed about an outer surface of the proximal end of the number sleeve 80. An outer diameter of the dose member 12 typically corresponds to and matches with the outer diameter of the housing 10. The dose member 12 is secured to the number 80 to prevent relative movement there between. The dose member 12 is provided with a central opening.

The trigger 11, also denoted as dose button is substantially T-shaped. It is provided at a proximal end of the injection device 1. A stem 64 of the trigger 11 extends through the opening in the dose member 12, through an inner diameter of extensions of the drive sleeve 30 and into a receiving recess at the proximal end of the piston rod 20. The stem 64 is retained for limited axial movement in the drive sleeve 30 and against rotation with respect thereto. A head 11c of the trigger 11 is generally circular. The trigger side wall 11b or skirt extends from a periphery of the head 11c and is further adapted to be seated in a proximally accessible annular recess of the dose member 12.

To dial a dose a user rotates the dose member 12. With the spring 40 also acting as a clicker and the clutch member 60 engaged, the drive sleeve 30 the spring or clicker 40, the clutch member 60 and the number sleeve 80 rotate with the dose member 12. Audible and tactile feedback of the dose being dialed is provided by the spring 40 and by the clutch member 60. Torque is transmitted through saw teeth between the spring 40 and the clutch member 60. The helical groove 81 on the number sleeve 80 and a helical groove in the drive sleeve 30 have the same lead. This allows the number sleeve 80 to extend from the housing 10 and the drive sleeve 30 to climb the piston rod 20 at the same rate. At a limit of travel a radial stop on the number sleeve 80 engages either with a first stop or a second stop provided on the housing 10 to prevent further movement. Rotation of the piston rod 20 is prevented due to the opposing directions of the overall and driven threads on the piston rod 20.

The last dose limiting member 35 keyed to the housing 10 is advanced along the threaded section 31 by the rotation of the drive sleeve 30. When a final dose dispensed position is reached, a radial stop formed on a surface of the last dose limiting member 35 abuts a radial stop on the flange portion 33 of the drive sleeve 30, preventing both, the last dose limiting member 35 and the drive sleeve 30 from rotating further.

Should a user inadvertently dial beyond the desired dosage, the injection device 1, configured as a pen-injector allows the dosage to be dialed down without dispense of the medicament from the cartridge 6. For this the dose member 12 is simply counter-rotated. This causes the system to act in reverse. A flexible arm of the spring or clicker 40 then acts as a ratchet preventing the spring 40 from rotating. The torque transmitted through the clutch member 60 causes the saw teeth to ride over one another to create the clicks corresponding to dialed dose reduction. Typically, the saw teeth are so disposed that a circumferential extent of each saw tooth corresponds to a unit dose.

When the desired dose has been dialed the user may simply dispense the set dose by depressing the trigger 11. This displaces the clutch member 60 axially with respect to the number sleeve 80 causing saw teeth thereof to disengage. However, the clutch member 60 remains keyed in rotation to the drive sleeve 30. The number sleeve 80 and the dose member 12 are now free to rotate in accordance with the helical groove 81.

The axial movement deforms the flexible arm of the spring 40 to ensure the saw teeth cannot be overhauled during dispense. This prevents the drive sleeve 30 from rotating with respect to the housing 10 though it is still free to move axially with respect thereto. The deformation is subsequently used to urge the spring 40 and the clutch member 60 back along the drive sleeve 30 to restore the connection between the clutch member 60 and the number sleeve 80 when the distally directed dispensing pressure is removed from the trigger 11.

The longitudinal axial movement of the drive sleeve 30 causes the piston rod 20 to rotate through the through opening of the support of the housing 10, thereby to advance the bung 7 in the cartridge 6. Once the dialed dose has been dispensed, the number sleeve 80 is prevented from further rotation by contact of a plurality of members extending from the dose member 12 with a corresponding plurality of stops. A zero dose position is finally determined by the abutment of one of axially extending edges of members of the number indicating sleeve 80 with a corresponding stop of the housing 10.

The expelling mechanism or drive mechanism 8 as described above is only exemplary for one of a plurality of differently configured drive mechanisms that are generally implementable in a disposable pen-injector. The drive mechanism as described above is explained in more detail e.g. in WO2004/078239A1, WO 2004/078240A1 or WO 2004/078241A1 the entirety of which being incorporated herein by reference.

The injection device and shown in FIG. 8 has a further feature compared to the device as described in any of WO2004/078239A1, WO 2004/078240A1 or WO 2004/078241A1. Here, the trigger 11 has a radially widened shoulder section 69 at or near a bottom of the axially elongated stem 64. The shoulder section 69 comprises a distally facing end face 67. The distal end face 67 is provided with a toothed structure 68. It may for instance comprise a crown wheel section to engage with a correspondingly shaped toothed structure 38 of the drive sleeve 30. The toothed structure 38 may be located at a proximal end or at a proximal end face 37 of the drive sleeve 30. The proximal end of the drive sleeve 30 may also comprise a radially widened shoulder 36 co-operating with the radially widened shoulder section 69 of the trigger 11.

In addition, there may be provided a compression spring 39 located axially between the button 11 and the dial member 12. In this way the trigger 11 is depressible in distal direction 2 against the action of the spring 39. In an initial configuration or in a dose setting configuration there is provided a small gap between the toothed structures 38 and 68 so that the trigger 11 is rotationally decoupled from the dial member 12. Upon depressing the trigger 11 in distal direction 2 for dispensing of a dose the trigger 11 is moved in distal direction 2 relative to the dial member 12 and against the action of the spring 39. It is then and due to the toothed structures 38 and 68 that the trigger 11 is rotationally locked to the drive sleeve 30. Since the drive sleeve 30 is rotationally locked to the housing 10 during those expelling or dose dispensing the trigger 11 is also rotationally locked to the housing 10 during the dose dispensing action.

When releasing the trigger 11 the spring 39 serves to displace the trigger 11 in proximal direction 3 and away from the dial member 12. The rotational interlock between the drive sleeve 30 and the trigger 11 is then abrogated and the trigger 11 may become freely rotatable relative to the housing 10 and relative to the dial member 12 as long as the drive mechanism 8 is in the dose setting mode.

Instead of mutually corresponding toothed structures 38 and 68 the proximal end face 37 and the distal end face 67 of the drive sleeve 30 and the trigger 11 may be provided with a friction enhanced surface finish. Then and during dose dispensing the trigger 11 may become rotationally locked to the drive sleeve 30 by way of a frictional engagement. In another embodiment, the trigger 11 may be permanently rotationally locked to the drive sleeve 30, e.g. through a splined engagement.

In FIG. 8 a further embodiment is illustrated providing a rotational interlock between the trigger 11 and the drive sleeve 30. Alternative to the toothed structures 38 and 68 there may be provided a toothed or splined structure 168 on the outer circumference of the stem 64 of the trigger 11 to rotationally engage with a correspondingly shaped toothed or splined structure 138 at an inside facing side wall section of the drive sleeve 30. The toothed or splined structure 168 of the trigger 11 may be arranged at an axial offset from the toothed or splined structure 138 of the drive sleeve 30. Upon depression of the trigger 11 towards the distal direction 2 the toothed or splined structure 168 may engage with the toothed or splined structure 138 thereby rotationally interlocking the trigger 11 to the drive sleeve 30.

Alternatively, it is also conceivable that the trigger 11 and the drive sleeve 30 are permanently interlocked by means of the toothed or splined structures 168 and 138. As an example, one of the toothed or splined structures 138, 168 may comprise a radially extending pin axially slidably engaged with a correspondingly shaped groove of the other one of the splined structures 138, 168. In this way, the trigger 11 and the drive sleeve 30 can be permanently rotationally locked.

Figure 10:
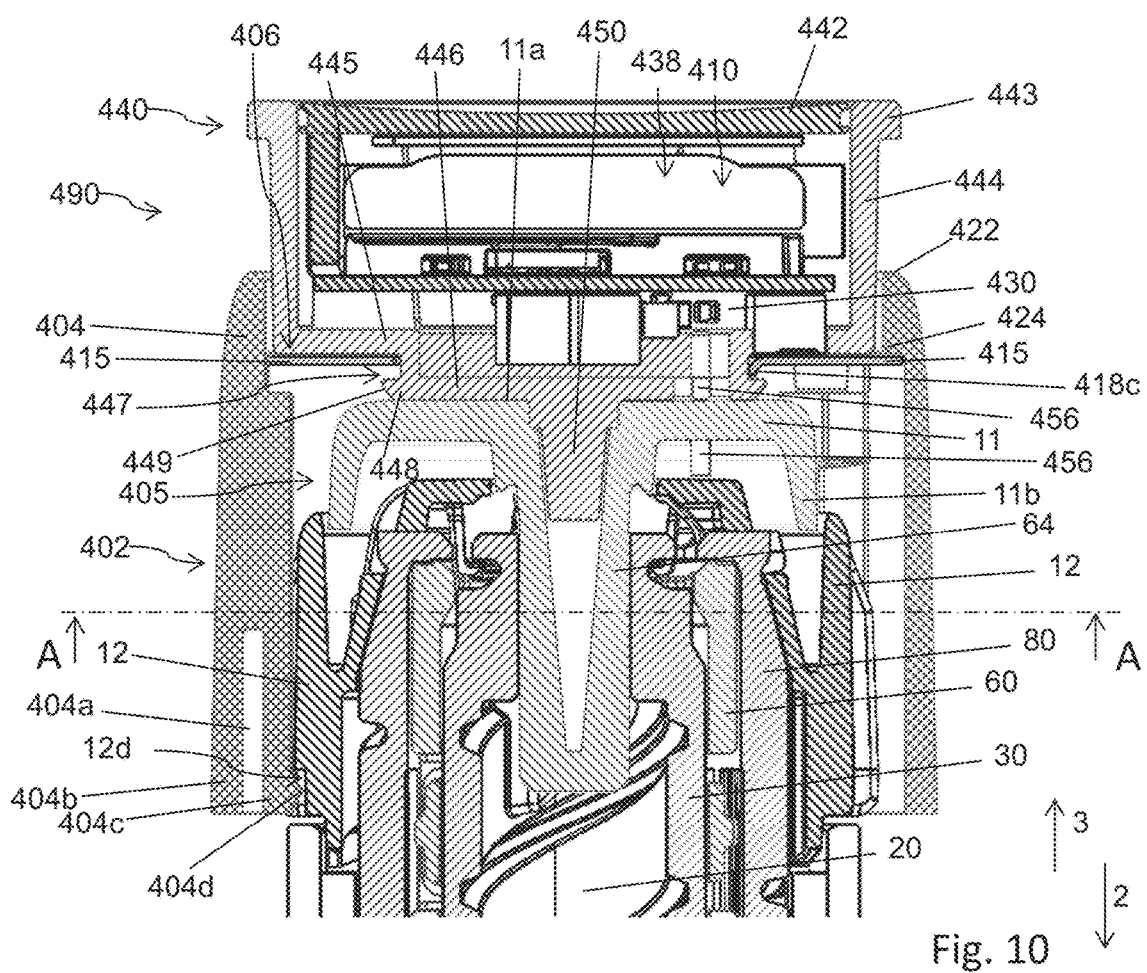
FIG. 10 is a cross-section through a proximal portion of an injection device with another example of a data collection device attached thereto.

The injection device as illustrated in FIG. 10 is substantially identical to the injection device as illustrated in FIG. 9. There are a few modifications compared to the example as shown in FIG. 8 in order to achieve a rotational coupling between the trigger 11 with an outer housing 10 of the injection device during dispensing of a dose.

Figure 18:
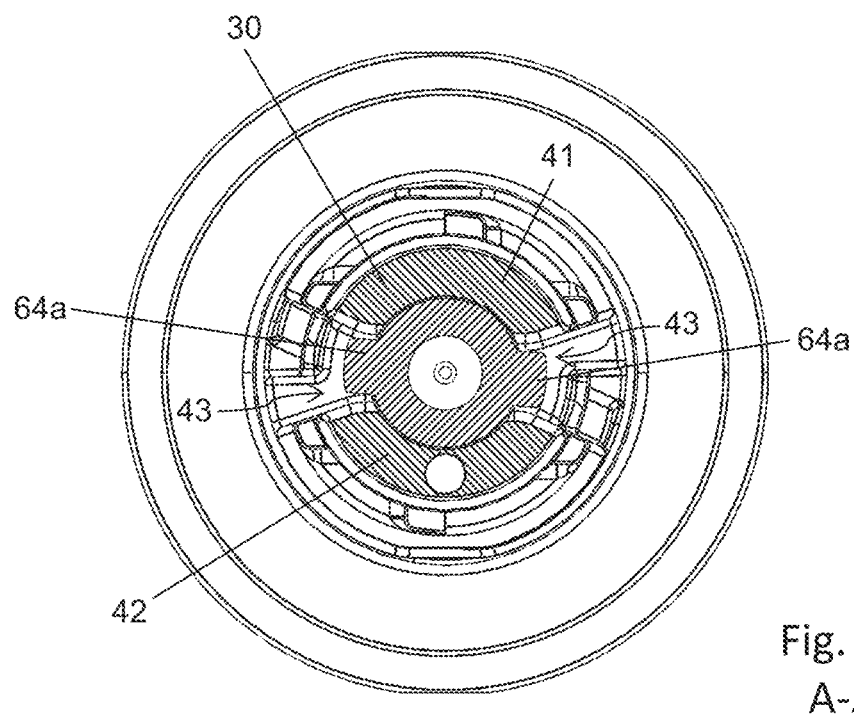
FIG. 18 is a cross-section through the injection device of FIG. 10 along A-A.
Figure 19:
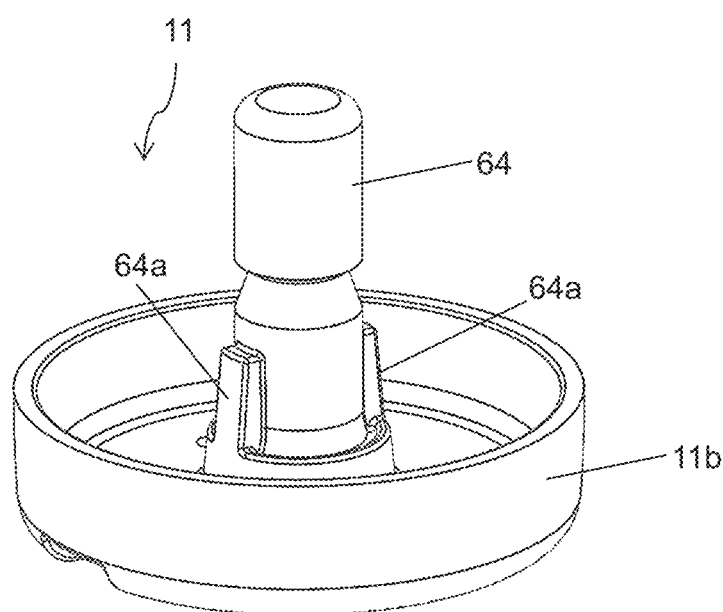
FIG. 19 is a perspective view of the trigger of FIG. 16 as seen from below.
Figure 20:
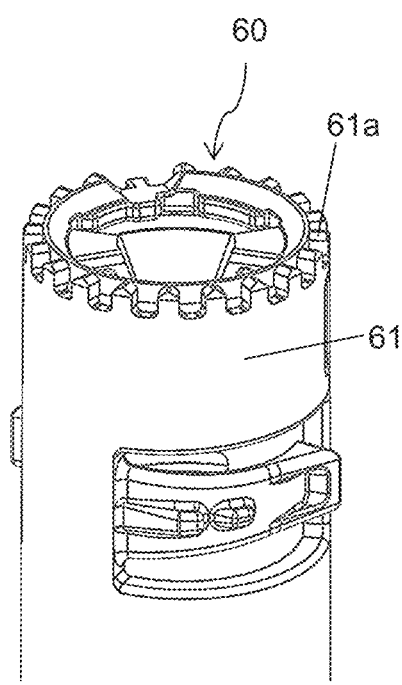
FIG. 20 is a perspective view of a proximal end of a clutch of the injection device.

As it is illustrated in FIGS. 18-20 in connection with FIG. 10 the clutch 60, which is radially sandwiched between a drive sleeve 30 and the dose dial 12, is free of any axial protrusions at its proximal end. As shown in FIG. 20 the proximal and upwardly pointing end of the clutch 60 comprises a tubular-shaped sidewall 61 with numerous teeth 61a pointing in axial direction and forming a toothed rim at a proximal end face of the clutch 60. Here, the tips of the various teeth 61a coincide with a proximal end face of the clutch 60.

This configuration of the clutch 60 enables a direct rotational engagement between the trigger 11 and the drive sleeve 30. As indicated in FIG. 18 the drive sleeve 30 comprises two oppositely located keying features 41, 42 with two oppositely located recesses 43 that are arranged circumferentially between the keying features 41, 42. The recesses 43 are located diametrically opposite to each other at the proximal end of the drive sleeve 30. The keying features 41, 42 comprise two longitudinally extending legs enclosing the longitudinally extending slit-shaped recesses 43 that are open towards the proximal end of the drive sleeve. The trigger 11 comprises a circular-shaped head 11c and an annular-shaped trigger sidewall 11b as illustrated in FIG. 19. In a radial center of the head 11c there protrudes a trigger stem 64 in axial direction as illustrated in FIG. 10.

The trigger stem 64 comprises two diametrically oppositely located keying features 64a. The keying features 64a are sized and shaped to fit into the recesses 43 between the keying features 41, 42 as illustrated in FIG. 18. The circumferential extension of the keying features 64a matches with the circumferential or tangential extension of the recesses 43. In this way, the button 11 can be rotationally locked to the drive sleeve 30. During a dose expelling operation the drive sleeve 30 is subject to a longitudinal displacement relative to the housing 10 but is hindered to rotate relative to the housing 10. In this way and due to the torque proof engagement between the drive sleeve 30 and the trigger 11 also the trigger 11 is hindered to rotate relative to the housing 10 during a dose expelling operation of the injection device 1.

Figure 16:
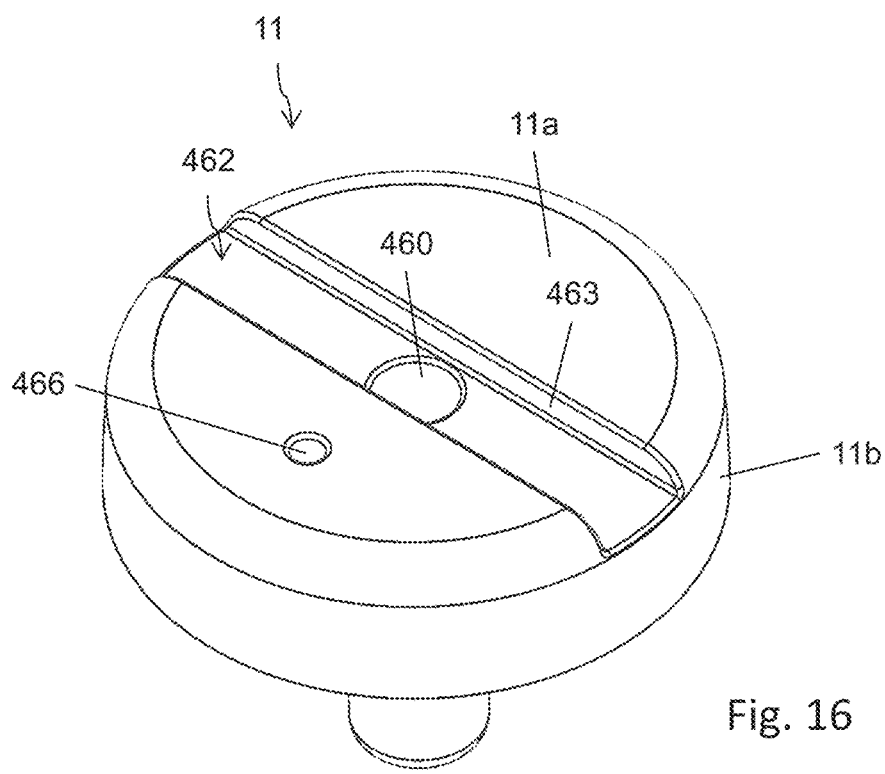
FIG. 16 is an isolated perspective view of a trigger of the injection device.

In FIG. 16, the trigger 11 is shown from the opposite outer side. The trigger 11 comprises a disc shaped trigger head 11c comprising a proximally facing trigger end face 11a. The trigger end face 11a comprises a torque transmission counter-structure 462. The torque transmission counter-structure 462 comprises an elongated recessed slot extending from one outer edge of the trigger end face 11a to an opposite outer edge of the disc-shaped trigger end face 11a.

In a radial center of the trigger end face 11a there is provided a button stem receptacle 460. The button stem receptacle 460 is located in the longitudinal or radial center of the torque transmission counter-structure 462. As illustrated in FIG. 16 the torque transmission counter-structure 462 comprises oppositely located longitudinal side edges 463 that are configured to engage with correspondingly-shaped side edges of a torque transmission structure 452 protruding from an outside of a bottom section 445 of a button 440 of the data collection device 400 that will be explained in detail with regard to FIGS. 10-15.

The button stem receptacle 460 may comprise a conical profile in axial direction. The button stem receptacle 460 may comprise a tapered and hence narrowing shape towards the distal direction 2 as illustrated in FIG. 10. On the bottom section 445 of the button 440 as illustrated in FIG. 15 there may be provided a button stem 450 comprising a correspondingly tapered or conical shape. The button stem 450 is sized to fit into the button stem receptacle 460 upon assembly of the data collection device 400 with the proximal end of the injection device, hence with the dial member 12. As further illustrated in FIG. 16 the trigger 11 also comprises a through opening 466 that is shaped and configured to receive a pin 456 of there through.

Figure 17:
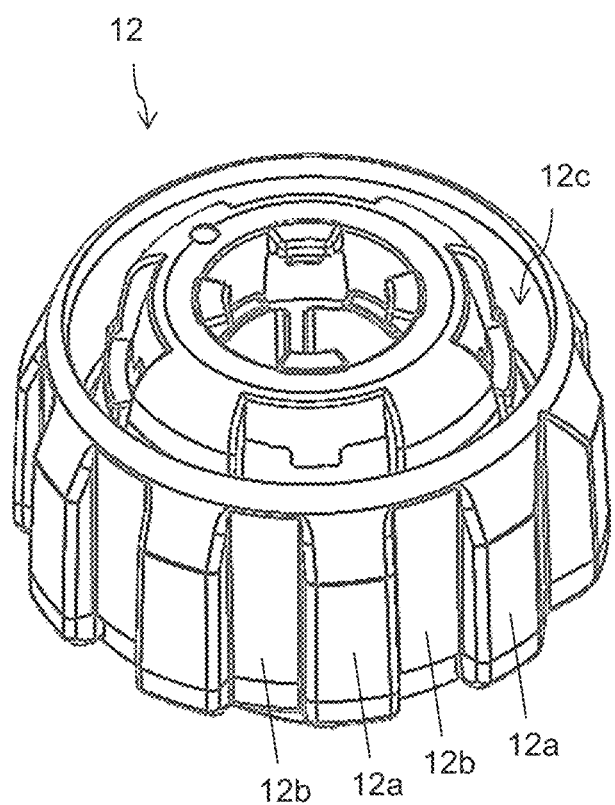
FIG. 17 is an isolated perspective view of the dial of the injection device.

The dial member 12, e.g. in form of a dial button, is illustrated in FIG. 17. The dial member 12 comprises an outer collar provided with numerous longitudinally extending radially protruding ribs 12a and longitudinally extending grooves 12b located between those ribs 12a. The arrangement of ribs and grooves 12a, 12b provides a unique encoding of the dial member 12 to engage with a correspondingly encoded sidewall 404 of a body 402 of the data collection device 400. In this way, the sidewall 404 and the body 402 of the data collection device 400 can be assembled slip free to the dial member 12 so as to enable a slip-free transmission of a torque to the dial member 12 when the body 402 of the data collection device should be subject to a rotation relative to the housing 10 while it is assembled to the dial member 12. On the outside of the body 402 there is provided a gripping surface 408 featuring numerous axially extending protrusions and/or grooves enabling a slip free gripping of the body 402.

In FIG. 17 the dial member 12 is shown from its proximal end. It comprises a groove-shaped annular receptacle 12c to receive a distally facing sidewall 11b provided at an outer edge of the trigger 11.

The shape and structure of the ribs 12a and grooves 12b on the outside circumference of the dial member 12 is unique and comprises a symmetry breaking feature which is identically provided on the inside of the sidewall 404 of the body 402 of the data collection device 400. In this way it is provided that the data collection device 400 and the body 402 can be only assembled to the dial member 12 in a single or unique orientation.

Figure 11:
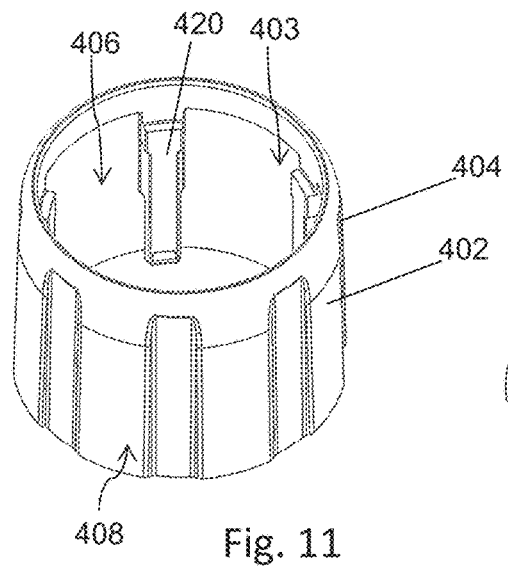
FIG. 11 is an isolated perspective view of a body of the data collection device.

The grooves 12b and the protrusions 12a ensure a rotational coupling when engaged with correspondingly-shaped protrusions 420 of the sidewall 404 as indicated in FIG. 11. There, the sidewall 404 comprises numerous radially inwardly extending and axially elongated protrusions 420 each of which being configured to engage with a groove 12b of the dial member 12.

As it is further illustrated in FIG. 10 the sidewall 404 of the body 402 comprises an elongated slit 404a adjacent to a distal end of the sidewall 404. The slit 404a divides the sidewall 404 into an outer section 404b and an inner section 404c. The inner section 404c comprises a radially inwardly extending protrusion on an inside of the sidewall 404 engaging with a correspondingly-shaped recess 12d on an outside surface of the dial member 12.

The recess 12d is shaped to receive the protrusion 404d. The protrusion 404d may snap fit with the recess 12d. The recess 12d may be located at a distal end of one of the elongated ribs 12a. By means of the protrusion 404d engaging with the recess 12d the body 402 axially engages with the dial member 12. In addition, the shape of the outer surface of the dial member 12 and the shape of an inside surface of the sidewall 404 may be configured to enable a frictional engagement between the sidewall 404 and the dial member 12 when the data collection device 400 is slipped over the dial member 12.

For instance, the dial member 12 and/or the protrusions 12a may comprise an elastomeric material, such as a rubber material exhibiting a comparatively high friction coefficient so as to enable and to support a friction fit or a clamp fit between the body 402 and the dial member 12.

The number, the shape and the orientation of the numerous protrusions 420 of the body 402 match with the shape, size and position or orientation of the grooves 12b of the dial member 12. In this way, a slip free and rotational coupling can be established between the body 402 and the dial member 12 as the data collection device 400 is assembled to the dial member 12. The protrusions 420 form or constitute a fastening portion 403 of the body 402. The inside surface of the sidewall 404 forms a receptacle section 405 to engage with the outside surface of the dose member 12.

The data collection device 400 comprises a body 402 that is configured for attachment to the dial member 12 of the injection device 1. The data collection device 400 further comprises a button 440 that is attached to the body 402. The button 440 is axially displaceable relative to the body 402. It is in a sliding engagement with the body 402. The button 440 is free to rotate relative to the body 402. The button 440 comprises a cup-shaped bottom part with a substantially planar-shaped bottom section 445 and a circumferential sidewall 444. The sidewall 444 is of tubular or cylindrical shape. It is unitarily or integrally formed with the bottom section 445.

Towards the top or towards the proximal direction the sidewall 444 comprises a radially outwardly extending collar 443. The radius or the outer circumference of the collar 443 is larger than the diameter of a through opening or recess 423 provided at a proximal end face 422 of the body 402. The sidewall 444 comprises an outer shape and a cross-section that is sized to fit into the recess 423 or through opening provided at the proximal end face 422 of the body 402. In this way the bottom 440 can be axially guided and moved into the body 402 until the collar 443 axially abuts against the proximal end face 422 of the body 402.

The button 440 forms a sensor housing 338 as illustrated in FIG. 13. The bottom section 445 and the sidewall 444 form a hollow receptacle to receive the entirety of the electronic components of the data collection device 400. The sensor housing 338 and hence the button 440 is covered with a planar-shaped top portion 441 serving as a lid. The top portion 441 may seal the interior of the button 440 and hence of the sensor housing 338. The sidewall 444 comprises at least one or several radially inwardly protruding flange portions 436 extending radially inwardly from the collar 443 into the interior of the sensor housing 338 as illustrated in FIG. 14. These radially inwardly protruding flange portions 436 are located at a predefined distance from the proximal end face of the collar 443. The predetermined distance substantially equals the material thickness of the top portion 441. The top portion 441 or the lid is configured to abut axially on the circumferentially distributed flange like protrusions 436. This enables a flush mounted assembly of the outside surface, hence of the button end face 442 with the enclosing collar 443. As illustrated in FIG. 10 any pressure can be kept away from the electronic components located inside the interior of the button 440.

Figure 12:
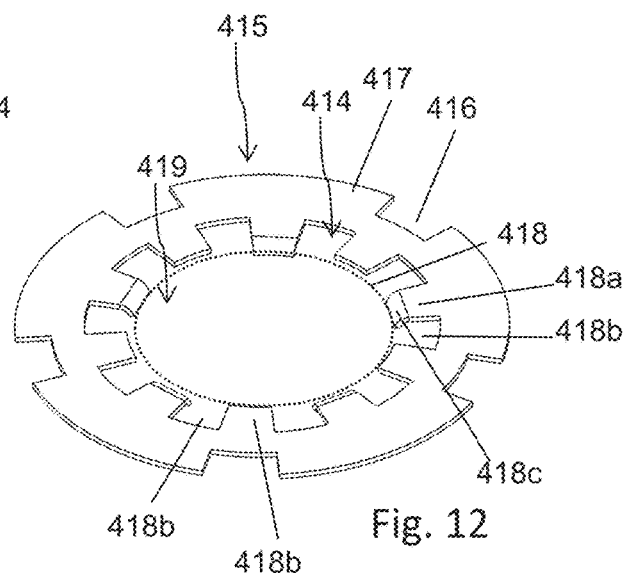
FIG. 12 is a perspective view of a scale disc.

The bottom section 445 of the button 440 comprises at least one through opening or window 434 that is aligned with the sensor 412. The sensor 412 may be implemented as an optical transmitter and receiver. It may comprise a light emitting diode (LED) and a photodiode. The arrangement of the sensor 412 above and in axial alignment with the through opening 334 allows for an unobstructed access or view to the scale 414 located underneath. The scale 414 comprises a scale disc 415 as illustrated in FIGS. 12 and 13. The scale disc 415 may comprise a metal or a plastic disc. It comprises a central circular through opening 419 with an inside edge 418. Towards the inside edge 418 there are provided numerous protrusions 418*a* and recesses 418*b*. The protrusions 418*a* and recesses 418*b* are arranged along the circumference of the inside edge 418 in an alternating order. The scale disc 415 may be formed from a metallic stamping or plastic molding process. Typically, the sensor 412 operates in the infrared spectral range. For this it is of benefit when the scale disc 415, at least its protrusions 418*a* comprise a comparatively high reflectivity in the infrared spectral range.

Every second radially inwardly extending protrusion 418*a* comprises a free edge 419*c* that is bended by about 90° in axial direction. In this way, the total axial dimensions of the scale disc 415 is somewhat enlarged in the region of the inside edge 418. Along the outside edge the scale disc 415 comprises numerous radial recesses 416 and protrusions 417. The recesses 416 match with the protrusions 420 on the inside of the sidewall 404 of the body 402. In this way, the scale disc 415 is configured to slide in longitudinal direction relative to the sidewall 404 and hence relative to the body 402.

On an outside or lower side of the bottom section 445 there is provided a circular-shaped socket section 446 protruding from the planar-shaped bottom section 445. The socket section 446 comprises a circumferential groove 447 configured to receive the protrusions 418*a* on the inside edge 418 of the scale disc 415. The axial dimension of the groove 447 matches with the axial extension or dimension of the bended free edges 418*c* of the scale disc 415. In this way and by means of only a few bended portions 418*c* the scale disc 415 can be axially secured to the socket section 446 of the button 440. In this way the scale disc 415 and hence the scale 414 is axially constrained to the button 440. The bended portions or bended free edges 419*c* of the radial protrusions 418*a* act as axial retention features that serve to bias the scale disc 415 in proximal direction 3 against the outside surface of the bottom section 445 of the button 440. This ensures a controlled axial gap between the sensor 412 and the scale disc 415.

The scale disc 415 is free to slide along the body 402 as the button 440 is displaced in axial direction relative to the body 402. Via the recesses 416 receiving the longitudinal protrusions 420 the scale disc 415 and hence the scale 414 is rotationally locked to the body 402.

In FIG. 12 there are illustrated numerous, e.g. ten protrusions 418*a* alternating with an equal number of recesses 418*b* in circumferential or tangential direction. In this way the alternating protrusions 418*a* and recesses 418*b* provide binary flags that are located at a radial position that overlaps with the radial position of the sensor 412. The sensor 412 located axially adjacent to the scale disc 415 is directed towards the inside edge 418 and hence to the alternating protrusions 418*a* and recesses 418*b* as the scale disc 415 is subject to rotation relative to the sensor 412. E.g. a number of ten pairs of alternating protrusions 418*a* and recesses 418*b* provides a resolution of 20 units per revolution.

As further illustrated in FIG. 10 the outer edge and hence the outer protrusions 417 of the scale disc 415 are configured to axially abut against an inwardly extending flange 424 provided near the proximal end of the sidewall 404. In this way and since this flange 424 comprises a surface normal pointing in distal direction the scale disc 415 is hindered to pass through the recess or through opening 423 provided at the proximal end of the body 402. Insofar the scale disc 415 provides a double function. It serves as a rotary encoder and prevents a disassembly of the button 440 from the body 402.

As further illustrated in FIG. 15 the socket section 446 comprises a radially widened disc portion 448 with a beveled edge 449. The disc portion 448 is located at a predefined axial distance from the bottom section 445. This axial distance defines the axial width of the groove 447. The beveled edge 449 enables a snap fit engagement of the scale disc 415 with the groove 447.

At the outside surface of the bottom section 445 there is further provided a torque transmission structure 452 in form of an elongated slot protruding axially from the socket section 446 and extending all across the socket section 446 in radial direction. The torque transmission structure 452 comprises oppositely located side faces 453. The torque transmission structure 452 is correspondingly and complementary-shaped to the torque transmission counter-structure 462 of the trigger 11.

When the injection device system 490 is appropriately assembled and when the data collection device 400 is correctly attached to the proximal end of the injection device 1 the torque transmission structure 452 is in torque-proof engagement with the torque transmission counter-structure 462. Here, the side faces 453 and 463 are in direct abutment so as to transfer an angular momentum or a torque across the interface of the trigger 11 and the button 440. Through the mutually engaging torque transmission structures 452, 462 and hence by the mutually engaging protruding and recessed slots a torque proof engagement of the button 440 and the trigger 11 is obtained. In this way the button 440 is hindered to rotate during a dose expelling action of the injection device.

In the radial center of the torque transmission structure 452 there is provided the button stem 450 comprising a somewhat conical structure and extending further distally away from the planar bottom section 445. The button stem 450 is configured to engage with the correspondingly-shaped button stem receptacle 460 provided in the trigger 11. The button stem receptacle 460 is formed in the stud 64, which at least in sections is hollow. The inside surface of the button stem receptacle 460 is of conical shape. The mutually conically-shaped button stem 450 and the-shaped button stem receptacle 460 are configured to establish a self-centering as the button stem 450 is inserted into the button stem receptacle 460 during assembly of the injection system 490, i.e. when attaching the data collection device 400 to the injection device 1. The torque transmission structure 452 comprises a male slot feature, whereas the trigger 11 and the torque transmission counter-structure 462 comprise a correspondingly-shaped female slot feature. The button stem may comprise a male spigot configured to provide a coaxial centering of the button 440 to the trigger 11.

As further illustrated in FIGS. 10 and 15 there is provided a flexible arm 455 on the bottom section 445 of the button 440. The flexible arm 455 comprises a free end with an axially extending pin 456. The pin 456 is shaped and configured to extend through the further through opening 466 provided in the trigger 11 as illustrated in FIG. 16. The pin 456 protruding the receptacle 466 is also illustrated in FIG. 10. As indicated there, the distal end of the pin 456 is in axial abutment with the dial member 12 even when the button 440 is in a proximal, hence dose dialing state. The pin 456 is operably connected with a switch 430 configured to switch on or to switch off the electronic components of the data collection device 400.

When the button 440 is depressed in distal direction 2, hence downward in FIG. 10 the button 440 and the button section 445 will exert a distally directed pressure to the trigger 11 thereby inducing a dose expelling action. With this motion the pin 456 cannot be displaced any further in distal direction relative to the dial member 12. Instead, the pin 456 will close or open a contact in a switch 430 located inside the button 440. Relative to the button 440, the pin 456 moves in proximal direction 3 because the button 440 is displaced in distal direction 2 relative to the housing 10 while the pin 456 cannot be displaced any further in distal direction due to the axial abutment with the dial member 12.

The sensor arrangement 410 comprises a printed circuit board (PCB). The PCB can be of rigid type with surface mounted components. It may comprise a coin cell or button battery.

The switch 430 may comprise a micro switch. As the pin 456 is subject to a proximally directed displacement relative to the button 440 the electronic components of the data collection device 400, in particular a processor arrangement 50 and the sensor arrangement 410 will be activated. As the dial member 12 starts to rotate during a dose expelling action the button 440 does not rotate and the rotation of the coded scale disc 415 that is rotationally coupled to the dial member 12 through the splined connection with the body 402 rotates relative to the sensor 412.

There may be provided two separate optical sensors inside the sensor housing 338. The two sensors 412 may be configured to provide an incremental quadrature signal that is processable by the processor arrangement 50, such as a micro controller to detect a direction of rotation and to count the number of changes of state during the rotation of the scale disc 415.

LIST OF REFERENCE NUMBERS 1 injection device
2 distal direction
3 proximal direction
4 dose incrementing direction
5 dose decrementing direction
6 cartridge
7 bung
8 drive mechanism
10 housing
11 trigger
11a trigger end face
11b trigger sidewall
11c head
11d recess
11e indentation
12 dial member
12a rib
12b groove
12c receptacle
12d recess
13 dosage window
14 cartridge holder
15 injection needle
16 inner needle cap
17 outer needle cap
18 protective cap
20 piston rod
21 bearing
22 first thread
22a display
23 pressure foot
24 second thread
25 barrel
26 seal
28 threaded socket
30 drive sleeve
31 threaded section
32 flange
33 flange
35 last dose limiting member
36 shoulder
37 proximal end face
38 toothed structure
39 spring
40 spring
41 keying feature
42 keying feature
43 recess
50 processor arrangement
52a memory unit
52b memory unit
53 switch
54 power source
55 timer
56a magnet
56b magnet
57 output
59 connection
60 clutch member
61 sidewall
61a tooth
62 insert piece
63 rib
64 stem
64a keying feature
65 external electronic device
66 data connection
67 distal end face
68 toothed structure
69 shoulder section
71a formation
71b formation
71c formation
80 number sleeve
90 dial extension
100 data collection device
102 body
103 fastening portion
104 sidewall
105 receptacle section
106 through opening
107 formation
108 flange portion
109 extension
110 sensor arrangement 112 sensor
114 scale
130 switch
131 switch component
132 switch component
138 toothed section
168 toothed section
190 injection system
200 data collection device
202 body
203 fastening portion
204 sidewall
205 receptacle section
206 through opening
208 flange portion
209 flange portion
210 sensor arrangement
212 sensor
214 scale
222 end face
223 recess
230 switch
240 button
242 button end face
243 collar
244 shaft
245 end section
260 scale drum
262 drum end face
264 friction enhancing structure
266 friction pad
268 sidewall
270 rotary bearing
290 injection system
300 data collection device
302 body
303 fastening portion
304 sidewall
305 receptacle section
306 through opening
308 flange portion
309 flange portion
310 sensor arrangement
312 sensor
314 scale
322 end face
323 recess
314 scale
340 button
342 button end face
343 collar
344 shaft
345 flange portion
360 end section
390 injection system
400 data collection device
402 body
403 fastening portion
404 sidewall
404a slit
404b outer section
404c inner section
404d protrusion
405 receptacle section
406 through opening
408 gripping surface
410 sensor arrangement
412 sensor
414 scale
415 scale disc
416 recess
417 protrusion
418 inside edge
418a protrusion
418b recess
418c bended portion
419 through opening
420 protrusion
422 end face
423 recess
424 flange
430 switch
436 protrusion
438 sensor housing
440 button
441 top portion
442 bottom end face
443 collar
444 sidewall
445 bottom section
446 socket section
447 groove
448 disc portion
449 beveled edge
450 button stem
452 torque transmission structure
453 side face
455 flexible arm
456 pin
460 button stem receptacle
462 torque transmission counter-structure
463 side face
466 through opening
490 injection system

The invention claimed is:

1. A data collection device attachable to an injection device, the data collection device comprising:
a body attachable to a dial member of the injection device, the injection device comprising a trigger, the dial member, and an expelling mechanism, the injection device being configured such that during expelling of a medicament by the injection device, (a) a relative rotation occurs between the dial member and the trigger upon an advancement of the expelling mechanism of the injection device, and (b) the trigger is rotationally fixed relative to a housing of the injection device;
a sensor arrangement comprising a sensor and a sensed element, wherein the sensor is configured to detect a rotation of the body relative to the trigger during expelling of the medicament;
a processor arrangement configured to determine, based on the detected rotation, an amount of the medicament expelled by the injection device; and
a button attached to the body, wherein the button is axially displaceable relative to the body and wherein the button is freely rotatable relative to the body.

2. The data collection device according to claim 1, wherein the body comprises a fastening portion with a cylindrically shaped sidewall forming a hollow receptacle section of the body, wherein the hollow receptacle section is configured to receive the dial member.

3. The data collection device according to claim 2, wherein the cylindrically shaped sidewall is provided with a friction enhancing structure so as to provide a slip free or clamped mechanical engagement and fastening of the body and the dial member.

4. The data collection device according to claim 1, wherein the button comprises an end section that is in axial abutment with an end face of the trigger when the data collection device is attached to the dial member.

5. The data collection device according to claim 1, wherein the sensor arrangement comprises one or more of an optical sensor, a magnetic sensor, a capacitive sensor, or a mechanical sensor.

6. The data collection device according to claim 1, wherein the sensed element comprises a magnetic code along a circumferential direction.

7. The data collection device according to claim 1, wherein the sensed element comprises magnets and the sensor arrangement is configured to vary an output due to variations in a magnetic field as the body rotates relative to the trigger during expelling of the medicament.

8. The data collection device according to claim 1, wherein the sensor arrangement includes a magnetic sensor and wherein the sensed element comprises a magnetic encoding.

9. The data collection device according to claim 1, wherein the sensed element comprises a scale disc comprising a magnetic encoding and the sensor is configured to detect a magnetization of portions of the scale disc.

10. The data collection device according to claim 1, wherein the sensor arrangement comprises an optical encoder, a light source, and a light detector.

11. The data collection device according to claim 1, wherein the sensor is arranged on or in the button and wherein the sensed element is arranged inside the body.

12. The data collection device according to claim 1, wherein the button comprises a sidewall and a bottom section forming an interior space to accommodate at least one of the sensor and the processor arrangement.

13. The data collection device according to claim 1, further comprising a switch configured to switch on or to switch off electronic components of the data collection device.

14. The data collection device according to claim 13, wherein the switch is configured to activate at least one of the sensor arrangement and the processor arrangement.

15. The data collection device according to claim 13, wherein the switch comprises one or more of a mechanical switch, an electrical switch, a magnetic switch, or an optical switch.

16. The data collection device according to claim 1, wherein one or more magnets are provided around a circumference of a side wall of the body.

17. An injection system comprising:
an injection device for expelling a number of user-selectable doses of a medicament, the injection device comprising:
an elongated housing extending along an axial direction and configured to accommodate a cartridge filled with the medicament and sealed by a bung that is displaceable in a distal direction for expelling of the medicament,
a dial member rotatable relative to the elongated housing during expelling of the medicament, and
a trigger displaceable in the axial direction relative to the dial member to initiate or to control expelling of the medicament, wherein the trigger is configured not to rotate relative to the elongated housing during expelling of the medicament; and a data collection device attachable to the injection device, the data collection device comprising:
a body attachable to the dial member,
a sensor arrangement comprising a sensor and a sensed element, wherein the sensor is configured to detect a rotation of the body relative to the trigger during expelling of the medicament,
a button attached to the body, wherein the button is axially displaceable relative to the body, and
a processor arrangement configured to determine, based on the rotation detected by the sensor, an amount of the medicament expelled by the injection device.

18. The injection system according to claim 17, wherein the trigger is coupled to a clutch provided to switch the injection device between a dose setting mode and a dose dispensing mode.

19. The injection system according to claim 17, wherein the button comprises an end section that is in axial abutment with an end face of the trigger when the data collection device is attached to the dial member.

20. The injection system according to claim 17, wherein the button the button is freely rotatable relative to the body of the data collection device.

21. The injection system according to claim 17, wherein one or more magnets are provided around a circumference of a side wall of the body.

22. An injection system comprising
an injection device comprising a trigger, a dial member, and an expelling mechanism, and the injection device being configured such that during expelling of a medicament by the injection device, (a) a relative rotation occurs between the dial member and the trigger upon an advancement of the expelling mechanism of the injection device, and (b) the trigger is rotationally fixed relative to a housing of the injection device; and
a data collection device comprising
a body attachable to the dial member of the injection device,
a button attached to the body, wherein the button is axially displaceable relative to the body and wherein the button is freely rotatable relative to the body and wherein the button comprises an end section that is configured to axially abut with an end face of the trigger,
a sensor arrangement comprising a sensor and a sensed element, wherein the sensor is configured to detect a rotation of the body relative to the trigger during expelling of the medicament, and
a processor arrangement configured to determine, based on the detected rotation, an amount of the medicament expelled by the injection device.

23. The injection system according to claim 22, wherein the end section is in axial abutment with the end face of the trigger when the data collection device is attached to the dial member.

24. The injection system according to claim 22, wherein one or more magnets are provided around a circumference of a side wall of the body.

25. A data collection device attachable to an injection device, the data collection device comprising:
a body attachable to a dial member of the injection device, the injection device comprising a trigger, the dial member, and an expelling mechanism, the injection device being configured such that during expelling of a medicament by the injection device, (a) a relative rotation occurs between the dial member and the trigger upon an advancement of the expelling mechanism of the injection device, and (b) the trigger is configured not to rotate relative to a housing of the injection device;

a button attached to the body, wherein the button is axially displaceable relative to the body and wherein the button is freely rotatable relative to the body;

a sensor arrangement comprising a sensor, wherein the sensor is configured to detect a rotation of the body relative to the button during expelling of the medicament; and a processor arrangement configured to determine, based on the detected rotation, an amount of the medicament expelled by the injection device.

26. The data collection device according to claim 25, wherein one or more magnets are provided around a circumference of a side wall of the body.

27. The data collection device according to claim 25, wherein the button comprises an end section that is configured to be in axial abutment with an end face of the trigger when the data collection device is attached to the dial member.

* * * * *

UNITED STATES PATENT AND TRADEMARK OFFICE
CERTIFICATE OF CORRECTION

| | | |
|---|---|---|
| PATENT NO. | : 12,214,174 B2 | Page 1 of 1 |
| APPLICATION NO. | : 17/737107 | |
| DATED | : February 4, 2025 | |
| INVENTOR(S) | : Maurice Toporek et al. | |

It is certified that error appears in the above-identified patent and that said Letters Patent is hereby corrected as shown below:

In the Claims

Column 48, Line 23, Claim 20, delete "the button the button" and insert -- the button --

Signed and Sealed this
Twenty-fifth Day of March, 2025

Coke Morgan Stewart
*Acting Director of the United States Patent and Trademark Office*